(12) United States Patent
Broberg et al.

(10) Patent No.: US 8,012,692 B2
(45) Date of Patent: Sep. 6, 2011

(54) ELASTIN PEPTIDE FINGERPRINTS AND ANALYSIS METHODS FOR MMP12 RELATED TO COPD

(75) Inventors: Per Broberg, Lund (SE); Thomas Fehniger, Lund (SE); György Marko-Varga, Lund (SE); Stephan Uebel, Martinsried (DE)

(73) Assignee: AstraZeneca AB (SE)

( * ) Notice: Subject to any disclaimer, the term of this patent is extended or adjusted under 35 U.S.C. 154(b) by 760 days.

(21) Appl. No.: 10/572,872

(22) PCT Filed: Sep. 24, 2004

(86) PCT No.: PCT/SE2004/001378
§ 371 (c)(1),
(2), (4) Date: Mar. 21, 2006

(87) PCT Pub. No.: WO2005/029090
PCT Pub. Date: Mar. 31, 2005

(65) Prior Publication Data
US 2006/0292631 A1    Dec. 28, 2006

(30) Foreign Application Priority Data
Sep. 25, 2003    (SE) ...................................... 0302559

(51) Int. Cl.
*G01N 33/68* (2006.01)
*G01N 30/72* (2006.01)
*A61K 38/39* (2006.01)
*C12N 9/50* (2006.01)

(52) U.S. Cl. .......... 435/7.1; 436/86; 436/173; 530/353; 435/219

(58) Field of Classification Search ................... 435/7.1, 435/219; 436/86, 173; 530/353
See application file for complete search history.

(56) References Cited

FOREIGN PATENT DOCUMENTS

| WO | WO 89/01625 | 2/1989 |
|---|---|---|
| WO | WO 91/18290 | 11/1991 |
| WO | WO 99/64626 | 12/1999 |
| WO | WO 02/50287 A2 | 6/2002 |
| WO | WO 02/056025 A2 | 7/2002 |

OTHER PUBLICATIONS

Sacha et al. "Rational design of tropoelastin peptide-based inhibitors of metalloproteinases", Achives of Biochemistry and Biophysics 2003, 409:335-340.*
Mecham et al. "Elastin degradation by matrix metalloproteinases," J Biol Chem 272(29):18071-18076, 1997.*
Taddese et al., "Mapping of macrophage elastase cleavage sites in insoluble human skin elastin," Matrix Biology 27:420-428, 2008.*
Joos et al., "The role of matrix metalloproteinase polymorphisms in the rate of decline in lung function", *Human Molecular Genetics* 11(5):569-576 (2002).
Wallace and Sandford, "Genetic Polymorphisms of Matrix Metalloproteinases", *Am J Pharmacogenomics* 2(3):167-175 (2002).
Van Baar, Ben L. M. et al., "Characterisation of botulinum toxins type A and B, by matrix-assisted laser desorption ionisation and electrospray mass spectrometry", *Journal of Chromatography A*, 970, pp. 95-115, (2002).

* cited by examiner

*Primary Examiner* — Rosanne Kosson
(74) *Attorney, Agent, or Firm* — Connolly Bove Lodge & Hutz, LLP

(57) ABSTRACT

Methods for producing and using protein/peptide fingerprints, allowing identification and investigation of disease-associated proteins/peptides that can be linked to specific drug targets, or to specific drug target combinations. The methods are particularly useful for studies relating to Chronic Obstructive Pulmonary Disease (COPD), especially for the enzyme MMP12.

5 Claims, 6 Drawing Sheets

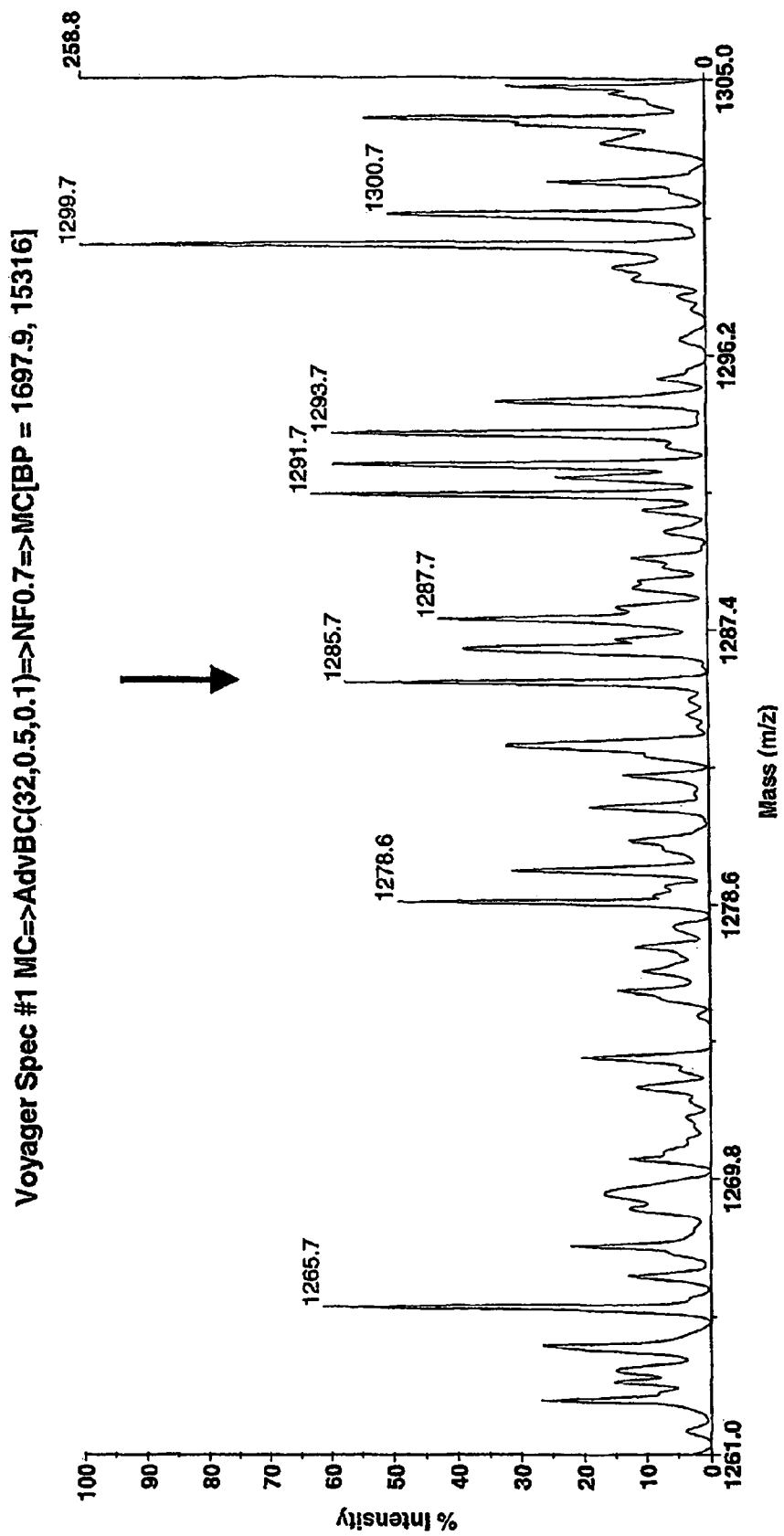

US 8,012,692 B2

ELASTIN PEPTIDE FINGERPRINTS AND ANALYSIS METHODS FOR MMP12 RELATED TO COPD

CROSS-REFERENCE TO RELATED APPLICATIONS

Figure 1A:
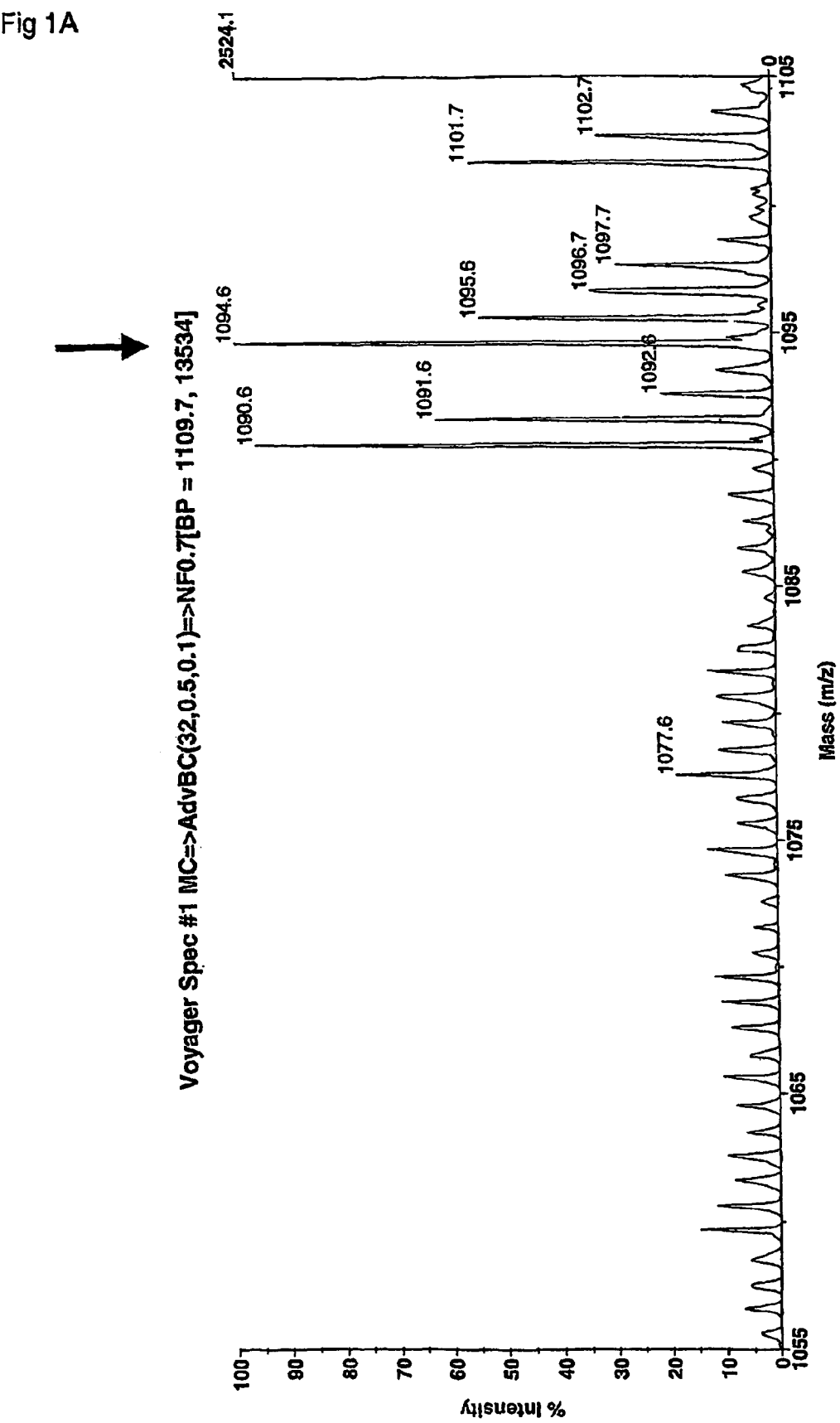

This application is a national phase application under 35 U.S.C. 371 of PCT International Application No. PCT/SE2004/001378, filed Sep. 24, 2004, which claims priority to Swedish Application Serial No. 0302559-0, filed Sep. 25, 2003.

FIELD OF THE INVENTION

The invention relates to methods for producing and using protein or peptide fingerprints, and to protein or peptide biomarkers. These methods and biomarkers may be used in the identification, evaluation, study or monitoring of conditions or diseases, for example to aid the discovery, development or use of drugs to treat those conditions or diseases.

BACKGROUND TO THE INVENTION

Various biological markers, known as biomarkers, have been identified and studied through the application of biochemistry and molecular biology to medical and toxicological situations. A biomarker has been described as "a characteristic that is objectively measured and evaluated as an indicator of normal biologic processes, pathogenic processes, or pharmacologic responses to a therapeutic intervention". A biomarker is any identifiable and measurable indicator associated with a particular condition or disease where there is a correlation between the presence or level of the biomarker and some aspect of the condition or disease (including the presence of, the level or changing level of, the type of, the stage of, the susceptibility to the condition or disease, or the responsiveness to a drug used for treating the condition or disease). The correlation may be qualitative, quantitative, or both qualitative and quantitative. Typically a biomarker is a compound, compound fragment or group of compounds. Such compounds may be any compounds found in or produced by an organism, including proteins (and peptides), nucleic acids and other compounds.

Biomarkers have a predictive power, and may be used to predict or detect the presence, level, type or stage of particular conditions or diseases (including the presence or level of particular microorganisms or toxins), the susceptibility (including genetic susceptibility) to particular conditions or diseases, or the response to particular treatments (including drug treatments). It is thought that biomarkers will play an increasingly important role in the future of drug discovery and development, by improving the efficiency of research and development programmes. Biomarkers can be used as diagnostic agents, monitors of disease progression, monitors of treatment and predictors of clinical outcome. For example, various biomarker research projects are attempting to identify markers of specific cancers and of specific cardiovascular and immunological diseases.

Proteomics (including peptidomics) technologies have been developed to analyse proteins (including peptides). These technologies are applied in a high-throughput mode, generating an enormous amount of data that is analysed using computer systems. Proteins from a biological sample are isolated and separated at a high resolution, for example by chromatographic separations. The set of proteins is then characterised using qualitative and quantitative techniques such as mass spectrometry. The result is a protein (or peptide) fingerprint (a constant, reproducible set of proteins or peptides). Selected proteins/peptides or groups of proteins/peptides may be analysed further to generate protein/peptide profiles. Proteomics is now viewed as the large-scale analysis of the function of genes and is becoming a central field in functional genomics.

Separation of proteins is commonly achieved using gel based techniques. 2D-PAGE (polyacrylamide gel electrophoresis) is currently the principal analytical method for studying the cellular expression of proteins. Instrumental platforms allow almost fully automated operations of 2D-gel analysis. The 2D-gel methods have good sensitivity and resolution for a large fraction of expressed proteins, typically those within a mass range of 10-120 kDa. However the methods have significant limitations in the identification of low abundance/low molecular weight proteins, some of which are present at concentrations as low as a few molecules per cell. Problems of sample loss and/or insufficient recovery have confounded the isolation of low abundance/low molecular weight proteins by 2D-PAGE. In addition, the presence of these proteins can be masked by the higher abundance protein spots. Other classes of proteins that are problematic for 2D-PAGE include acidic, basic, hydrophobic and high molecular weight proteins.

Multidimensional HPLC (High Performance Liquid Chromatography) has been used as a good alternative for separating proteins or peptides unsuited to 2D-PAGE. The protein or peptide mixture is passed through a succession of chromatographic stationary phases or dimensions which gives a higher resolving power. HPLC is also more flexible than the 2D-gel separation methods since the stationary and mobile phases can be selected for their suitability in resolving specific protein or peptide classes of interest and for compatibility with each other and with downstream mass spectrometric methods of detection and identification. On-line configurations of these types of multi-mechanism separation platforms are known.

Mass spectrometry (MS) is also an essential element of the proteomics field. In fact MS is the major tool used to study and characterise purified proteins in this field. The interface link in proteomics and MS, displaying hundreds or thousands of proteins, is made by gel technology where high resolution can be reached on a single gel. Researchers are successfully harnessing the power of MS to supersede the two-dimensional gels that originally gave proteomics its impetus.

The application and development of mass spectrometry (MS) to identify proteins or peptides separated via liquid phase separation techniques and/or gel-based separation techniques have led to significant technological advance in protein and peptide expression analysis. There are two main methods for the mass spectrometric characterization of proteins and peptides: matrix-assisted laser desorption ionization (MALDI) and electrospray ionization (ESI). Using various approaches, MALDI and ESI ion sources can be combined with time-of-flight (TOF) or other types of mass spectrometric analyzers to determine the masses or the sequences of peptides.

In MALDI, peptides are co-crystallized with the matrix, and pulsed with lasers. This treatment vaporizes and ionizes the peptides. The molecular weights (masses) of the charged peptides are then determined in a TOF analyzer. In this device, an electric field accelerates the charged molecules toward a detector, and the differences in the length of time it takes ionized peptides to reach the detector (their time-of-flight) reveal the molecular weights of the peptides; smaller peptides reach the detector more quickly. This method generates mass profiles of the peptide mixtures—that is, profiles of the molecular weights and amounts of peptides in the mixture. These profiles can then be used to identify known proteins from protein sequence databases.

In ESI and a technique called liquid chromatography (LC)/MS/MS, a voltage is applied to a very fine needle that contains a peptide mixture. The needle then sprays droplets into a mass spectrometric analyzer where the droplets evaporate and peptide ions are released. In LC/MS/MS, researchers use microcapilliary LC devices to initially separate peptides.

Mass spectrometry (MS) is a valuable analytical technique because it measures an intrinsic property of a bio-molecule, its mass, with very high sensitivity. MS can therefore be used to measure a wide range of molecule types (proteins, peptide, or any other bio-molecules) and a wide range of sample types/biological materials. Correct sample preparation is known to be crucial for the MS signal generation and spectra resolution and sensitivity. Sample preparation is therefore a crucial area for overall feasibility and sensitivity of analysis.

Proteins occur naturally within cells, as components of cellular structures and as components of natural biological fluids such as blood, urine, saliva, tears, lymph and sweat. Proteomics is an essential tool for studying biological systems and processes because proteins provide a rich source of valuable information. For example, this information allows the comparison of biomarkers that may differ qualitatively and/or quantitatively between healthy and diseased population groups. Proteomics technologies allow the identification of individual protein species in complex mixtures of proteins.

Proteomics are being used in drug discovery and development, for example to detect proteins significantly altered in patients with particular conditions or diseases. Some of these disease-associated proteins may be identified as novel drug targets and some may be useful as biomarkers of disease progression. Such biomarkers may be used to improve clinical development of a new drug or to develop new diagnostics for the particular disease.

Detection of disease-associated proteins may be achieved by the following method. Protein samples are taken from both diseased subjects and healthy subjects. These samples may be cells, tissues, or biological fluids that are processed to extract and enrich protein and/or peptide constituents. Typically the process entails partitioning into solution phase but may also include the establishment of protein and/or peptide components attached to solid matrixes. After high-throughput separation and analysis (proteomics), protein expression fingerprints are produced for either diseased or healthy subjects by qualitative and quantitative measurement. These fingerprints may be used as unique identifiers to distinguish individuals and/or establish and/or track certain natural or disease processes. These prototype fingerprints are established for each individual sample/subject and are recorded as numerical values in a computer database. The fingerprints are then analysed using bioinformatic tools to identify and select the proteins or peptides that are present in the prototype forms and whose expression may or may not be differentially present in the samples derived from the healthy and diseased subject samples. These proteins/peptides are then further characterised and detailed profiles are produced which identify the characteristic masses and physical properties of the proteins or peptides. Either a singular proteins/peptide or groups of proteins/peptides may be determined to be significantly associated with certain natural or diseased processes.

Various disease-associated proteins are known, and some of these are enzymes whose activity increases or decreases at some stage in the development of a particular condition or disease. Such enzymes may be suitable drug targets, leading to a search for pharmaceutically-active compounds (drugs) that could be used to inhibit or stimulate the enzyme and thus prevent or treat the condition or disease. Other disease-associated proteins may be degradation products of particular enzymes, or proteins that are made more abundantly in the presence of the disease.

Examples of disease-associated proteins include the metalloproteinases, a superfamily of proteinases (enzymes) believed to be important in a plethora of physiological disease processes. Modulation of the activity of one or more metalloproteinases may well be of benefit in these diseases or conditions. A number of metalloproteinase inhibitors are known (see for example the reviews of MMP inhibitors by Beckett R. P. and Whittaker M., 1998, Exp. Opin. Ther. Patents, 8(3):259-282, and by Whittaker M. et al, 1999, Chemical Reviews 29(9):2735-2776). Based on structural and functional considerations metalloproteinase enzymes have been classified into families and subfamilies as described in N. M. Hooper (1994) FEBS Letters 354:1-6. Examples of metalloproteinases include the matrix metalloproteinases (MMPs) such as the collagenases (MMP1, MMP8, MMP13), the gelatinases (MMP2, MMP9), the stromelysins (MMP3, MMP10, MMP11), matrilysin (MMP7), metalloelastase (MMP12), enamelysin (MMP19), and the MT-MMPs (MMP14, MMP15, MMP16, MMP17).

Examples of disease-associated proteins include those enzymes that have been implicated in the onset and/or progression of Chronic Obstructive Pulmonary Disease (COPD), as discussed below.

COPD, which is mainly caused by cigarette smoking, is expected to be the third leading cause of death worldwide by the year 2020. COPD is characterised by reduced maximum expiratory flow and slow forced emptying of the lungs. These airflow limitations are mainly due to chronic bronchitis, involving hypertrophy of mucous glands, and emphysema produced by destruction of alveolar walls. The latter leads to enlargement of the air spaces distal to the terminal bronchiole, with consequent collapse of small airways, limitations of the airflow, destruction of parts of the capillary bed, and loss of the elastic recoil of the lung. This loss of elastic recoil and the enlargement of the air spaces in the lungs of COPD patients lead to reduced values of forced expiratory volume (FEV), and increased values of forced vital capacity (FVC). Disease severity is determined as the degree of lung function impairment, which is measured with a spirometer. The presence of a postbronchodilator $FEV_1$<80% of the predicted value in combination with an $FEV_1/FVC$<70% confirms the presence of airflow limitation that is not fully reversible. The chronic exposure to cigarette smoke causes an inflammatory response in the lung, leading to changes in the airway epithelial surface and to activation and an increased number of several inflammatory cells.

Inflammation and a protease-antiprotease imbalance have long been proposed to act as downstream effectors of the lung destruction following chronic cigarette smoking. Histological studies have demonstrated increased numbers of macrophages and T-lymphocytes in the airways of smokers, and also an increase of neutrophils in the airways of smokers and COPD patients, which related to the severity of the airway obstruction. Alveolar macrophages are long-lived phagocytes, and are the most abundant defence cells in the lung both under normal conditions and during chronic inflammation. By sending out chemotactic factors they then recruit neutrophils and lymphocytes by activating adhesion molecule expression on pulmonary microvascular endothelial cells at the site of infection. The inflammatory cells invading the smoker's lung produce mediators locally, such as cytokines, serine- and metalloproteases, and oxidants. These mediators, which likely play an important role in the development of COPD, can act to further activate the inflammatory response, and also to degrade the components of the extracellular matrix.

Normally plasma proteinase inhibitors, especially $\alpha_1$-antitrypsin ($\alpha_1$-AT), prevent proteolytic enzymes from digesting structural proteins of the lung. According to the proteinase-antiproteinase hypothesis, emphysema result from an increase of proteinase release in the lungs, a reduction in the antiproteinase defense, or a combination. Elastin is the principal component of elastic fibres constituting a main part of the lung's extracellular matrix. Studies show that individuals who are homozygous for $\alpha_1$-AT deficiency have an increased susceptibility for developing pulmonary emphysema, especially if they also smoke.

One example of a disease-associated enzyme linked to COPD is the matrix metalloproteinase MMP12, also known as macrophage elastase or metalloelastase. One of MMP12's natural substrates is elastin, the insoluble, elastic protein of high tensile strength found in intercellular spaces of the connective tissues of large arteries, trachea, bronchi and ligaments. MMP12 was initially cloned in the mouse by Shapiro et al [1992, Journal of Biological Chemistry 267: 4664] and then in man by the same group (Shapiro et al, "Cloning and characterization of a unique elastolytic metalloproteinase produced by human alveolar macrophages", 1993, Journal of Biological Chemistry 268 (32): 23824-23829). The protein sequence of a human MMP12 is stored in the SwissProt database available at http://us.expasy.org/sprot/(swissprot: locus MM12_HUMAN, accession P39900). MMP-12 is preferentially expressed in activated macrophages, and has been shown to be secreted from alveolar macrophages from smokers [Shapiro et al, 1993, Journal of Biological Chemistry, 268: 23824-23829] as well as in foam cells in atherosclerotic lesions [Matsumoto et al, 1998, Am J Pathol 153: 109]. A mouse model of chronic obstructive lung disease (COPD) is based on challenge of mice with cigarette smoke for six months, two cigarettes a day six days a week. Wildtype mice developed pulmonary emphysema after this treatment. When MMP12 knock-out mice were tested in this model they developed no significant emphysema, strongly indicating that MMP-12 is a key enzyme in the COPD pathogenesis. MMP12 is believed to degrade lung tissue by degrading the elastin within the tissue. The role of MMPs such as MMP12 in COPD (emphysema and bronchitis) is discussed in Anderson and Shinagawa, 1999, Current Opinion in Anti-inflammatory and Immunomodulatory Investigational Drugs 1(1): 29-38. It was recently discovered that smoking increases macrophage infiltration and macrophage-derived MMP-12 expression in human carotid artery plaques Kangavari [Matetzky S, Fishbein M C et al., Circulation 102:(18), 36-39 Suppl. S, Oct. 31, 2000].

The current use of proteomics or peptidomics in drug discovery and development (particularly for the disease COPD) is limited by various factors, including for example:
a) the lack of profiles of disease-associated peptides that can be linked to specific drug targets (because current fingerprinting methods analyse total protein differences, and do not focus on a particular protein/drug target);
b) the lack of biomarkers to identify COPD sufferers at an early stage of the disease;
c) the lack of biomarkers to evaluate potential drugs that are MMP12 inhibitor compounds, particularly in clinical studies (ie for validation that the MMP12 target is hit by the inhibitor).

SUMMARY OF THE INVENTION

We have now developed a new methodology for producing and using protein/peptide fingerprints, allowing us to identify and investigate disease-associated proteins/peptides that can be linked to specific drug targets (such as MMP12), or to specific drug target combinations.

BRIEF DESCRIPTION OF THE TABLES AND FIGURES

Table 1 shows the MS atomic mass unit identities of 97 peptides resulting from digestion of elastin by MMP12 and separation by column chromatagraphy.

Table 2 shows the MS atomic mass unit identities of 185 peptides resulting from digestion of elastin by MMP12 and separation by column chromatagraphy.

Figure 1B:
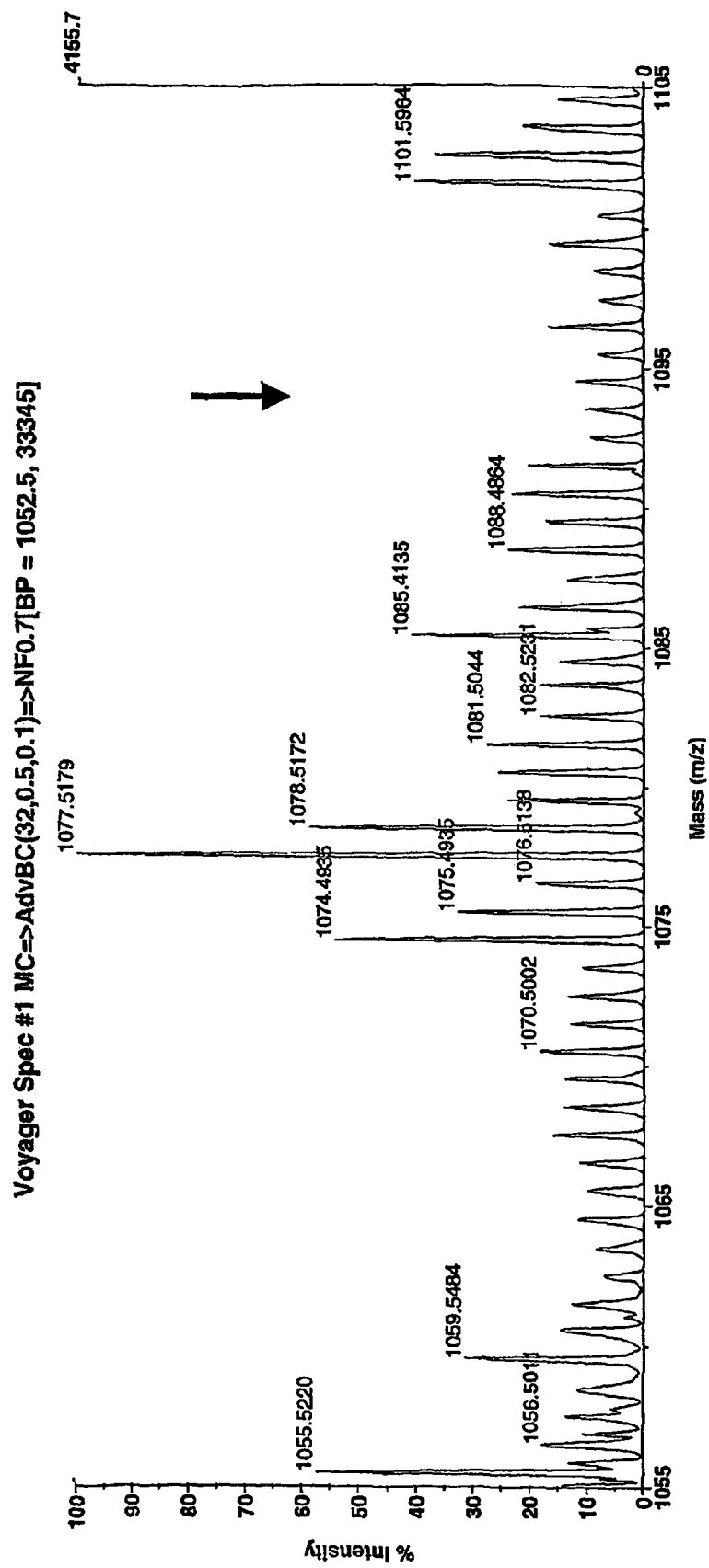
Figure 1C:
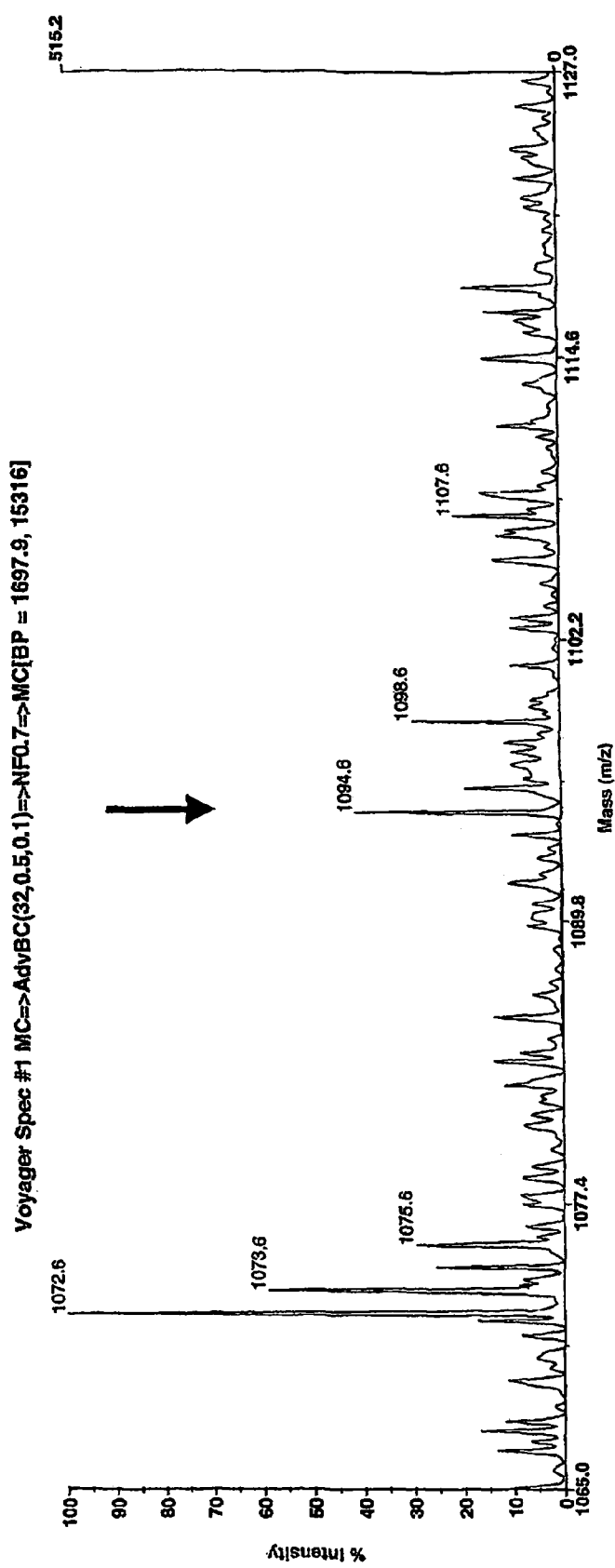

FIG. 1 shows the mass spectrum generated from a given liquid phase separation fraction where: FIG. 1A shows the peptide fingerprint in a human urine fraction from a COPD sufferer; FIG. 1B shows the peptide fingerprint in a healthy subject; FIG. 1C shows the peptide fingerprint in a MMP-12+ elastin mixture, 2.5 h incubation.

Figure 2A:
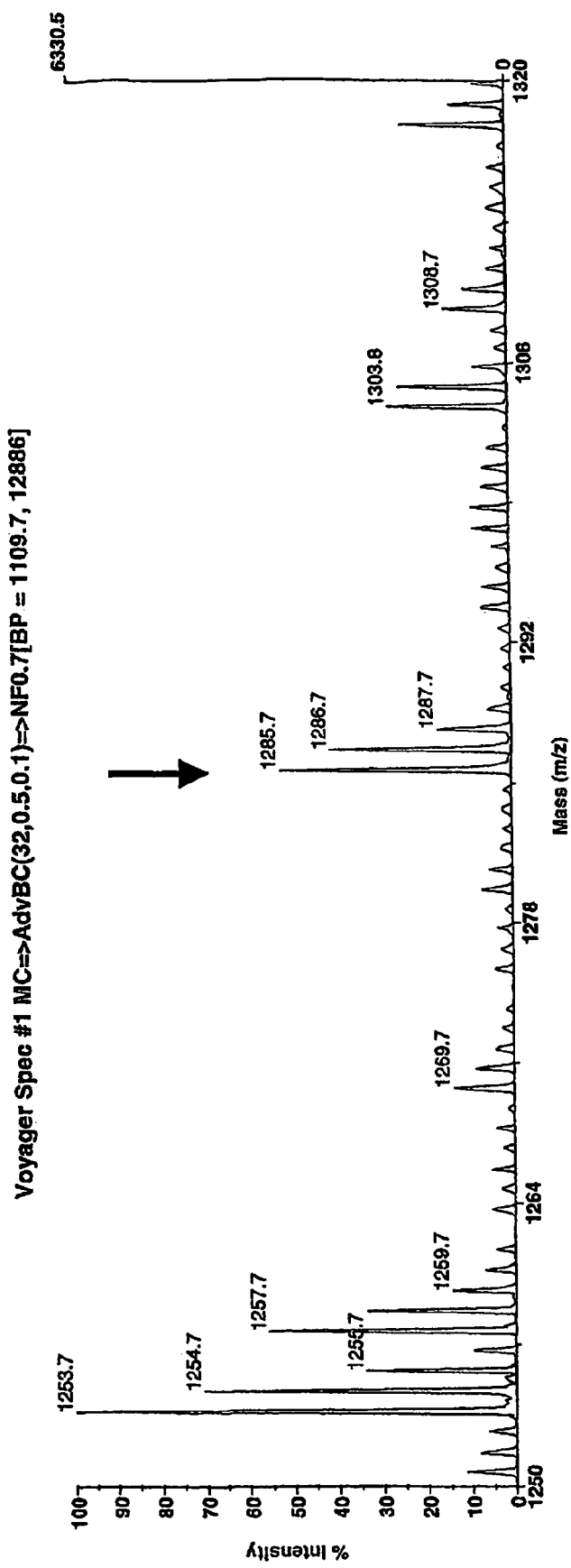
Figure 2B:
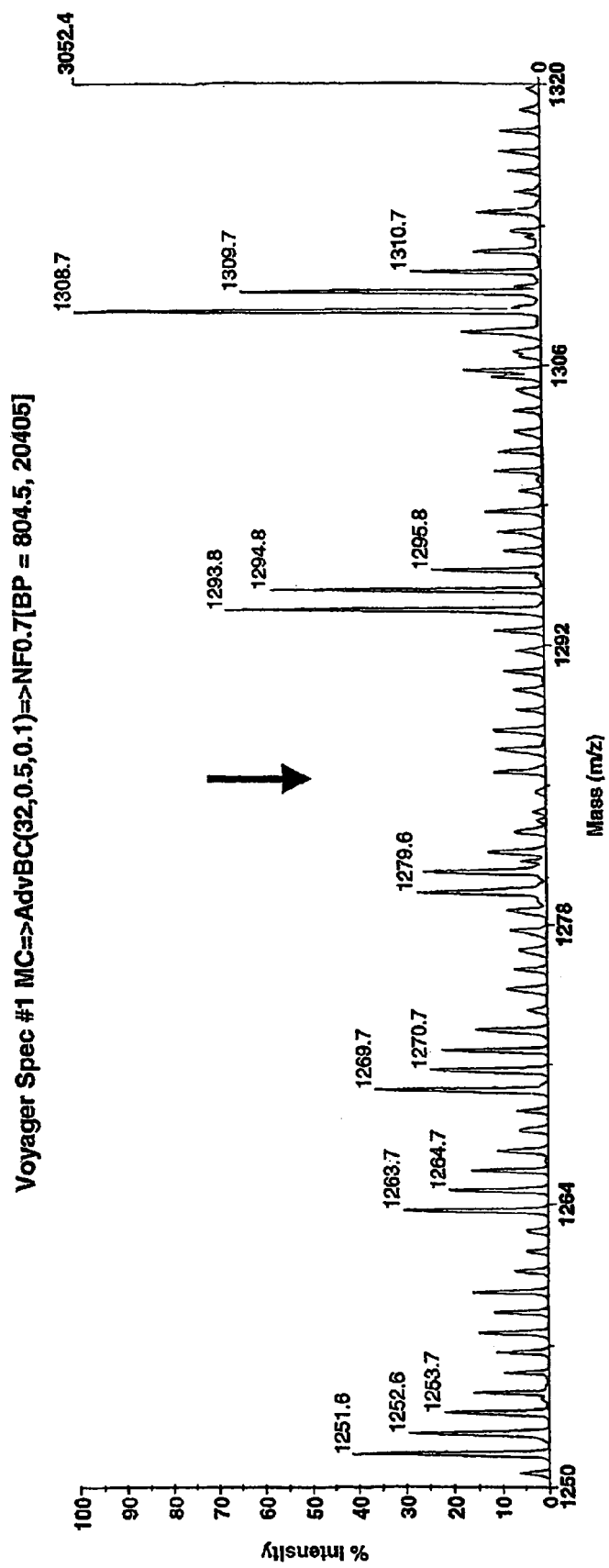

FIG. 2 is another example showing shows the mass spectrum generated from a given liquid phase separation fraction where: FIG. 2A shows the peptide fingerprint in a human urine fraction from a COPD sufferer; FIG. 2B shows the peptide fingerprint in a healthy subject; FIG. 2C shows the peptide fingerprint in a MP-12+ elastin mixture, 2.5 h incubation.

DETAILED DESCRIPTION OF THE INVENTION

We now provide a new method, composed of multiple linked steps, for detecting the naturally occurring products of protein expression and protein catabolism. This method may be used for biomedical evaluation and biomedical characterization.

The method may be applied to naturally occurring substances or mixtures of naturally occurring substances and synthetic substances. The method results in the identification of specific protein substituents, also known as peptides, present as separate entities or present within complex mixtures of proteins and peptides. Each peptide may be defined by a specific sequence of amino acids in alignment.

The method may quantitatively and qualitatively measure either the presence or absence of the peptides within complex mixtures of proteins and peptides. The method may be applied for the biomedical study of the relationships between the expression and function of proteolytic enzymes and the status of protein degradation products, hereafter referred to as unique peptides.

The method allows the identification of some or all peptides which are proteolytic breakdown products of a given enzyme with a given substrate and which are measurable (for example using MS identification).

The method combines several key steps together which results in the specific separation, isolation, and identification of unique peptides present in biological material. The unique peptides are the constituent units of protein molecules identifiable for example by MS or other methodologies.

The method may be applied to human clinical samples. The method may also be applied to samples derived from non-human animals.

We provide a multi-step method for identifying:
1) the unique peptide identity presented for example as atomic mass units of entities resulting from the proteolytic interaction of a given proteolytic-enzyme with its given substrate;
2) the preparation, separation, and identification of peptides derived from given proteolytic enzymes with given substrates either occurring naturally or produced in a laboratory setting;
3) the presence and/or absence of these same exact peptides in biological samples, for example within a sample of human blood or urine;
4) the statistical method for determining the identification of either naturally occurring peptides partitioned into fractions by the separation methodology referred to in 1) to 3) above;
5) the statistical method for defining the presence and/or absence of these same peptides in multiple human subjects, collected and grouped by, for example clinical disease status.

The method may be used to determine whether certain proteolytic enzyme processes are occurring or have occurred in human subjects, or in non-human animals. This may allow association of the presence and/or absence of certain products of proteolytic digestion, for example peptide fingerprints, in certain persons, or persons with known diseases, or persons with known stages or phases of disease. The method may allow measurement of the presence or absence or quantity of specific peptide fingerprints within human clinical samples such as for example urine or blood.

The method may allow monitoring of the effect of certain and or all medicines or substances which effect the expression or function of proteolytic enzymes. The method may allow us to measure the presence or absence or quantity of specific peptide fingerprints within human clinical samples such as for example urine or blood as a result of medical and or pharmacological intervention.

The method first identifies all or some of the peptides produced by a given enzyme with a given substrate in a controlled laboratory setting. This step optimizes the chances for producing all likely candidate peptide fragments from a given enzyme-substrate reaction. This includes attention to Michalis Minton kinetics for maximizing the ratio of reactants, the pH level and salt concentrations used in the reactant solutions, the temperature of the reaction, the time of the reaction, for example. This may result in the production of stable end form unit length entities of unique peptides which are present in the reactant solution [Reaction product 1]. The net result of the optimised laboratory controlled reaction of the given enzyme with the given substrate is a signature peptide profile for that reaction. This collection of unit length peptides resulting from proteolytic digestion is also referred to as a peptide fingerprint. Scheme A (below) illustrates this step (generation and identification of peptide entities, peptide fingerprint, and unique peptide atomic mass identification as products of laboratory controlled digestion of human protein substrates with given protein enzyme):

The peptide fingerprint is then subjected to a series of biochemical separation steps (described below) to fractionate the individual unique peptides by their intrinsic bio-physical properties, for example charge, size, and hydrophobicity properties. The individual fractions of the unique peptide fingerprint are then identified using MALDI MS to determine precise atomic mass measurements for each unique peptide entity. The net result of this fractionation and identification process is a quantitative and qualitative list of all peptide fragments produced and comprising the peptide fingerprint [Reaction product 2]. This list of atomic mass identities is then used in further steps of the method according to the invention.

In a first aspect of the invention, we provide a method to generate a peptide fingerprint of the degradation products of a disease-associated enzyme X, wherein enzyme X is associated with disease Y, which comprises:
 (a) mixing a disease-associated enzyme X with its natural substrate in vitro in conditions that allow interaction between enzyme X and its substrate;
 (b) allowing the substrate to be degraded by enzyme X;
 (c) analysing the mixture to produce a peptide fingerprint of the degradation products.

The peptide fingerprint produced by the method of the invention may be used in the diagnosis or study of disease Y, for example to aid the discovery and development and administration of drugs to treat disease Y, particularly drugs wherein enzyme X is the drug target.

Disease Y is any condition or disease affecting humans or non-human animals. In particular, disease Y is any condition or disease affecting humans. For example, disease Y may be a condition or disease affecting the respiratory tract (such as COPD), the cardiovascular system, the gastrointestinal tract, the neurological system, the endocrinological system, the immunological system. In addition, disease Y may be an allergic condition or disease, an infectious condition or disease, or an oncological condition or disease.

The disease-associated enzyme X is any enzyme that shows increased activity during the onset or progression of any condition or disease affecting humans and non-human animals (particularly humans). This increased activity causes or contributes to disease onset or progression. The disease-associated enzyme X may be a drug target.

The degradation products in the mixture will be peptides generated by breakdown of the substrate by the enzyme. The mixture is analysed by peptidomics technologies to produce a peptide fingerprint which we define as a constant, reproducible set of the degradation products. The peptide fingerprint and/or selected peptides or groups of peptides may be useful as biomarkers relating to disease Y (including its presence, its development and/or its treatment).

To determine the entities within the peptide fingerprint and produce Reaction Product 2 (see scheme A above), the peptides produced as Reaction Product 1 are first separated (for example, by chromatographic separation, liquid phase separations) utilising mechanisms such as:
A) size exclusion (in samples where fractionation is required based upon size);
B) hydrophobic interactions (utilisation of reversed phase separation mechanisms whereby peptides will be separated by hydrophobicity);
C) polar interactions (silanol and other types of polar functionalities readily interact with polar peptides and can be separated due to polar chromatographic interactions);
D) chiral affinity (chiral small molecules may be used as selective ligands for peptide binding and thus separation);
E) metal affinity (chelation by metal ion interaction of amine, and or carboxy-hydroxy functional groups, as well as Nickel ion-Histidine peptide residues, iron-, Gallium-ions and phosphate functionalities on peptides);

F) antibody binding (traditional antibody-antigen immunoaffinity bindings with both weak-medium-strong affinities, with binding constants ranging from $10^5$ to $10^{10}$).

After separation, the peptides are profiled by ascertaining their physiochemical properties plus accurate masses (the peptide index, comprising the size, polarity/charge and hydrophobicity of the peptides). This is optionally followed by sequencing of the peptides.

Scheme B below illustrates the technology platform for analysis of unique peptide fingerprints resulting in individual mass identities of peptide entities:

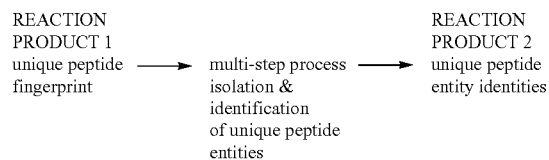

The method according to the first aspect of the invention may be used to identify biomarkers for a particular disease Y that is known to be associated with a particular drug target (enzyme X). The peptide fingerprint of the degradation products is used as a biomarker for disease Y.

In preferred methods according to the first aspect of the invention: enzyme X is any one of MMP2, MMP3, MMP7, MMP9, MMP12, and MMP14; the natural substrate is elastin; disease Y is COPD. In particularly preferred methods according to the second aspect of the invention, enzyme X is MMP12 (most preferably human MMP12), the natural substrate is elastin (most preferably human elastin) and disease Y is COPD.

As an example of a method according to the first aspect of the invention, monocyte elastase (comprised partly or wholly of MMP12) is mixed with human elastin. In this method, the disease-associated enzyme X is MMP12 which has the natural substrate elastin and is associated with COPD. Conditions are optimised to ensure high MMP12 activity and good degradation of elastin. Michaelis-Menten kinetics are used to determine the preferred stoichiometry of reactants, and the substrate type and amount are chosen to give a favourable equilibrium constant for the progress of the reaction.

A particular method according to the first aspect of the invention is a method to generate a specific peptide fingerprint composed of certain identified peptide products resulting from is the degradation of a substrate by the catalytic activity of enzyme X, wherein enzyme X is associated with a clinical condition known as disease Y, which comprises:

(a) mixing a disease-associated enzyme X in partially purified form or purified form with its natural substrate in vitro in conditions that allow interaction between enzyme X and the substrate;

(b) allowing the substrate to be selectively degraded by enzyme X;

(c) separating the individual components derived from the biochemical interaction of enzyme X with the substrate, and any groupings of the components selected in the steps (a) and (b) using chromatography procedures;

(d) analysing the products of degradation of the substrate by multi-step chromatography on specially prepared resins to produce fractions of the total peptide components of the substrate;

(e) detecting and identifying the individual component peptide/s derived from the substrate present in the selective process steps using mass spectrophotometry platforms including MALDI, SELDI and derivations of said platforms;

(f) assigning, to each detected peptide produced in steps (a) to (e), physical characteristics relating to size, charge, hydrophobicity, atomic mass and time of flight which are unique characteristics of the mass spectrophotometry analyses that can be related back exclusively to the peptide so that the peptide can be repetitively identified with the same and specific physical characteristics;

(g) identifying all peptides with mass characteristics in all fractions of the separation named above in steps (a) to (d);

(h) collecting all peptide identities into lists of identity.

The identities of peptides detected by the above method are peptide fingerprints of the substrate, and may be used either as isolated peptides or as collections of peptides. Such fingerprints may be used to identify, measure, monitor, and compare the activities of enzyme X with the substrate. In a preferred method, enzyme X is human MMP12, the substrate is human elastin, and the clinical condition known as disease Y is COPD.

We herein provide a peptide fingerprint comprising peptide products resulting from the degradation of elastin by the enzyme MMP12, wherein the peptide fingerprint comprises one or more of the peptides identified in Table 2. We also provide a peptide fingerprint comprising peptide products resulting from the degradation of elastin by the enzyme MMP12, wherein the peptide fingerprint comprises at least twenty of the peptides identified in Table 2. We further provide a peptide fingerprint comprising peptide products resulting from the degradation of elastin by the enzyme MMP12, wherein the peptide fingerprint comprises at least ninety of the peptides identified in Table 2. We also provide a peptide fingerprint comprising peptide products resulting from the degradation of elastin by the enzyme MMP12, wherein the peptide fingerprint comprises at least one hundred and fifty of the peptides identified in Table 2. A preferred peptide fingerprint comprises all the peptides identified in Table 1. Another preferred peptide fingerprint comprises all the peptides identified in Table 2.

Any and all combinations of the peptides identified by mass in Table 2 or Table 1 may be used in applications which measure or monitor the presence and/or absence of the protein elastin in any diagnostic setting of a clinical condition. Such clinical conditions include systemic inflammation, vascular inflammation, pulmonary inflammation, hepatic inflammation, cardiac inflammation, or other diseases which can be linked to the long term use of cigarettes or to the exposure to cigarette smoke. In particular, such clinical conditions include COPD. Any and all combinations of the peptides identified by mass in Table 2 or Table 1 may be used in any modified form including chemical modifications of constituent moieties, cross linking to moieties, labelling with moieties including radionuclides, fluorochromes, or like reagents. Any and all combinations of the peptides identified by mass in Table 2 or Table 1 may be used in diagnostic test kits which measure or monitor the presence or absence of the protein elastin.

In a second aspect of the invention, we provide a method to determine if or confirm that an enzyme X is associated with disease Y which comprises:

(a) obtaining a healthy biofluid sample or a healthy tissue sample;

(b) analysing the healthy sample to produce a healthy peptide fingerprint;

(c) obtaining a diseased biofluid sample or a diseased tissue sample, wherein the diseased sample shows signs of the onset or progression of disease Y;
(d) analysing the diseased sample to produce a diseased peptide fingerprint;
(e) comparing the healthy peptide fingerprint to the diseased peptide fingerprint and identifying the set of peptides found in the diseased peptide fingerprint;
(f) mixing enzyme X with its natural substrate in vitro in conditions that allow interaction between enzyme X and the substrate under optimal conditions;
(g) allowing the substrate to be degraded by enzyme X;
(h) analysing the mixture to produce a peptide fingerprint of the degradation products;
(i) comparing the diseased set of peptides identified in step (e) with the peptide fingerprint of the degradation products produced in step (h), and determining if there are statistically significant similarities or differences between them based upon qualitative and quantitative comparison using statistical formulations testing chance occurrence;
(j) if there are significant associations between the quantitative and qualitative parameters of measurement in the detected set of peptides identified in step (e) and the peptide fingerprint of the degradation products produced in step (h), concluding that enzyme X is associated with disease Y in the sample analysed;
(k) if there are no statistically significant similarities between the set of peptides identified in step (e) and the peptide fingerprint of the degradation products produced in step (h), concluding that enzyme X is not associated with disease Y in the sample analysed.

In a biofluid or tissue sample, enzyme X will have a defined selectivity for the substrate under the conditions used, in relationship to other enzymes in the sample. These other enzymes may or may not have degradative activity against the specific, natural substrate used in steps f-h of the above method. In a biofluid or tissue sample, the peptide fingerprint which results from the enzymatic cleavage of the natural substrate in the presence of enzyme X and these other enzymes will be distinct from the peptide singletons or groups of peptides resulting from the reaction in step h of the above method.

In a method according to the second aspect of the invention, human clinical material is analysed using the methodology described below. The quality of the human clinical material is an important factor in obtaining accurate measurements. The methods for accurately determining, identifying, or measuring unique peptide entities in human clinical material are directly dependent upon certain criteria. Quality is defined in relation to human clinical material as follows. Clinical samples should be obtained using methods which preserve the integrity of proteins in a natural state, and minimize the effects of denaturation, and destruction. This includes careful sample preparation, and storage under conditions which preserve protein structure and function. Human clinical material should be well documented in the features of clinical presentation which these samples represent. Information which relates the sample to specific aspects of the disease such as the clinical presentation of disease, for example stages or phases of disease, or noted impairments of structure and function characteristic or not of these diseases. Samples from subjects should be identifiable for example as being free or not free from obvious diseases. When possible the best practice should be the linkage of disease with the individual samples, and with other subject samples with similar linkages to disease. When possible the best practice should be the linkage of a particular site or location of disease with the individual samples When possible the best practice is to obtain as much information regarding the sample, the history of the sample, and the medical classification of the sample as possible. It is also important to obtain as much information as possible regarding the phases of disease reflected in individual samples.

Scheme C below illustrates the preferred description of quality human clinical samples:

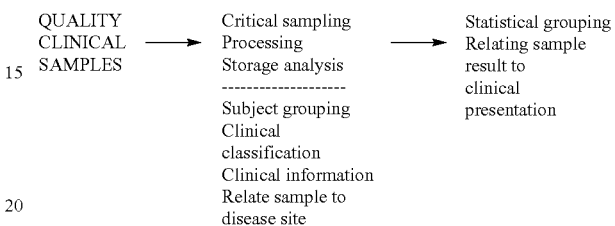

The biofluid or tissue sample may be derived from any part of the human or non-animal body (including cells grown in vitro), preferably from any part of the human body. For example, the sample may be derived from urine, blood, sputum, saliva, nasal secretions, exhaled breath condensate, bronchioalveolar fluid, bronchial fluid or any other biological fluid or tissue. A tissue sample is defined as a sample comprising one or more cells and their constituent parts in any infinite division. A biofluid is defined as any sample of clinical material in solution form (preferably human clinical material). This may include blood, serum, plasma, saliva, lavages, tears, urine, seminal fluid, joint fluid, aqueous humor, washings of cavities or sinuses, the soluble form of tissue preparations, the soluble form of organ preparations, or sweat. The samples may be derived from singular subjects or pools of singular samples from multiple subjects.

As defined herein, healthy biofluid or tissue samples are samples from individuals without recognised clinical disease or symptoms of disease. Healthy biofluid or tissue samples may represent the average or normal variation of expression of gene products in the human population that do not show any signs of disease onset or progression. As defined herein, diseased biofluid or tissue samples are samples from specific identified individuals that have been clinically evaluated and diagnosed for specific disease processes, or who show symptoms of clinical disease which are not yet categorised clinically as a specific disease. Diseased biofluid or tissue samples may express qualitatively and/or quantitatively different sets of peptides/proteins/endogenous products from healthy biofluid or tissue samples. Such differences include changes in the steady state, changes in destructive processes present in resident and non-resident cells, changes in differentiation states and changes in repair processes. Differentiation states are defined as stages of maturity in cell function and/or phenotype.

The biofluid or tissue samples are obtained by acquiring, processing and preparing the biological material. The methods according to the invention may be used for both small is scale and large scale clinical investigation, for example with prototype subject/patient groups of 10-20 patients or more in each study group. The clinical study material needs to be of high quality and this is ensured by optimised sampling, sample handling, and sample storage protocols. These sample protocols ensure the minimum degradation of the naturally occurring proteins and peptides present within these samples.

The biofluid or tissue samples and the enzyme/substrate mixture are analysed by peptidomics technologies to produce peptide fingerprints. These peptide fingerprints are obtained as explained above for the method according to the first aspect of the invention (peptide separation by various mechanisms followed by determination of physiochemical properties plus accurate masses, optionally followed by sequencing of the peptides).

When comparing the diseased set of peptides identified in step (e) with the peptide fingerprint of the degradation products produced in step (h), it is necessary to determine if there are statistically significant similarities or differences between them.

The diseased peptide profile may show individual variation based on sample type, the clinical development of disease, and the individual variations in metabolism by the enzymes being measured within the diseased biofluid or tissue sample. It is possible to generate peptide profiles from prototype samples showing a singleton peptide or number of peptides comprising the peptide fingerprints characteristic of early stage disease, mild disease, moderate disease or severe disease. Thus pathological and histological presentation of a disease may be linked to peptide profiling.

The diseased peptide profile may also differ depending on the source of the diseased biofluid or tissue sample. It is possible to generate peptide profiles from samples taken from different compartments of the human or non-animal body.

The diseased peptide profile may also differ depending on the individual human or non-human animal from which the sample was derived, or on the particular grouping of clinical is phenotype to which the human or non-human animal belongs.

In a variation of the method according to the second aspect of the invention, multiple biofluid or tissue samples are used wherein each diseased sample has the same disease.

In another variation of the method according to the second aspect of the invention, multiple disease sets are used (by using more than one sample each having a different disease, or by using one sample having more than one disease).

Combined analysis of diseased peptide profiles may be used to reduce a multifactorial disease processes to its component parts. Each part and its relation to other parts may be analysed.

In preferred methods according to the second aspect of the invention: enzyme X is any one of MMP2, MM3, MMP7, MMP9, MMP12, and MMP14; the natural substrate is elastin; disease Y is COPD. In particularly preferred methods according to the second aspect of the invention, enzyme X is MMP12 (most preferably human MMP12), the natural substrate is elastin (most preferably human elastin) and disease Y is COPD.

A preferred method according to the second aspect of the invention is a method to determine if or confirm that the enzyme MMP12 is associated with disease Y which comprises:

(a) obtaining a healthy biofluid sample or a healthy tissue sample;
(b) analysing the healthy sample to produce a healthy peptide fingerprint;
(c) obtaining a diseased biofluid sample or a diseased tissue sample, wherein the diseased sample shows signs of the onset or progression of disease Y;
(d) analysing the diseased sample to produce a diseased peptide fingerprint,
(e) comparing the healthy peptide fingerprint to the diseased peptide fingerprint and identifying the set of peptides found in the diseased peptide fingerprint;
(f) comparing the diseased set of peptides identified in step (e) with a peptide fingerprint comprising peptide products resulting from the degradation of elastin by the enzyme MMP12, wherein the peptide fingerprint comprises one or more of the peptides identified in Table 2, and determining if there are statistically significant similarities or differences between them based upon qualitative and quantitative comparison using statistical formulations testing chance occurrence;
(g) if significant associations between the quantitative and qualitative parameters of measurement are determined in step (f), concluding that the enzyme MMP12 is associated with disease Y in the sample analysed;
(h) if no significant associations between the quantitative and qualitative parameters of measurement are determined in step (f), concluding that the enzyme MMP12 is not associated with disease Y in the sample analysed.

Preferably disease Y is COPD. The peptide fingerprint comprising peptide products resulting from the degradation of elastin by the enzyme MMP12 preferably comprises at least twenty of the peptides identified in Table 2, or at least ninety of the peptides identified in Table 2, or at least one hundred and fifty of the peptides identified in Table 2.

Most preferably the peptide fingerprint comprises all the peptides identified in Table 1 or all the peptides identified in Table 2.

A particular method according to the second aspect of the invention is a method to determine if or confirm that an enzyme X is associated with a clinical condition known as disease Y which comprises:

a) obtaining a biofluid sample from healthy subjects ("healthy biofluid sample");
b) analysing the healthy biofluid sample by separation procedures to produce fractions of individual and collections of individual peptides;
c) detecting and identifying the peptide components in all fractions or a selected fraction containing components of the healthy biofluid sample;
d) assigning physical characteristics to each peptide or group of peptides relating to size, charge, hydrophobicity, atomic mass and time of flight which are unique characteristics of the mass spectrophotometry analyses that can be related back exclusively to the identified peptide so that the peptide can be repetitively identified with the same and specific physical characteristics;
e) identifying all peptides with mass characteristics in all fractions of the separation named above in steps (a) to (d) above;
f) forming all identified peptides in all fractions into a peptide fingerprint of that specific healthy biofluid sample ("healthy peptide fingerprint");
g) obtaining a diseased biofluid sample or a diseased tissue sample, wherein the diseased sample shows signs of the onset or progression of the clinical condition known as disease Y ("diseased biofluid sample);
h) analysing the diseased biofluid sample by separation procedures to produce fractions of individual and collections of individual peptides;
i) detecting and identifying the peptide components in all fractions or selected fractions containing components of the diseased biofluid sample;
j) assigning physical characteristics to each peptide or group of peptides relating to size, charge, hydrophobicity, atomic mass and time of flight which are unique characteristics of the mass spectrophotometry analyses that can be related back exclusively to the identified peptide so that the peptide can be repetitively identified with the same and specific physical characteristics;
k) identifying of all the peptides with mass characteristics in all fractions of the separation named above in steps (g) to (j) above;
l) forming all identified peptides in all fractions into a peptide fingerprint of that specific diseased biofluid sample ("diseased peptide fingerprint");
m) comparing the healthy peptide fingerprint to the diseased peptide fingerprint and identifying the individual components of singular peptides or sets of peptides found or differentially expressed in either the healthy or diseased peptide fingerprint;
n) mixing enzyme X with its natural substrate in vitro in conditions that allow interaction between enzyme X and its substrate;
o) allowing the substrate to be degraded by enzyme X;
p) analysing the enzyme X-substrate mixture to produce a peptide fingerprint of the degradation products ("substrate fingerprint");
q) comparing the set of peptides identified in step (m) with the substrate fingerprint produced in step (p) and, determining if statistically significant relationships exist in presence and absence and quantity between the set of peptides and the substrate fingerprint;
r) if statistically significant similarities are found in step (q), concluding that peptides produced by and identified as being associated with the interaction of enzyme X with the substrate are present, absent, or quantified in bio samples collected from subjects with a clinical condition known as disease Y;
s) if no statistically significant similarities are found in step (q), concluding that enzyme X is not associated with the clinical condition known as disease Y.

In a preferred method, the enzyme X is MMP12, the substrate is elastin, and the substrate fingerprint comprises one or more of the peptides identified in Table 2. In particular the substrate fingerprint comprises at least twenty of the peptides identified in Table 2. More particularly the substrate fingerprint comprises at least ninety of the peptides identified in Table 2. Most particularly the substrate fingerprint comprises at least one hundred and fifty of the peptides identified in Table 2. A preferred substrate fingerprint comprises all the peptides identified in Table 1. Another preferred substrate fingerprint comprises all the peptides identified in Table 2.

In a third aspect of the invention, we provide a method to determine the presence of the peptide fingerprint in clinical samples which comprises:
(a) obtaining a biofluid sample or a tissue sample;
(b) analysing the sample to obtain its peptide fingerprint;
(c) mixing enzyme X with its natural substrate in vitro in conditions that allow interaction between enzyme X and its substrate, wherein enzyme X is associated with disease Y;
(d) allowing the substrate to be degraded by enzyme X;
(e) analysing the mixture to produce a peptide fingerprint of the degradation products;
(f) comparing, in quantitative and qualitative terms of mass, elution time, solubility, time of flight and physical presence or abundance in relationship to other peptides, the peptide fingerprint of the sample identified in step (b) with the peptide fingerprint of the degradation products produced in step (e), and determining if there are statistically significant similarities and differences between the prototype subject/sample peptide fingerprints;
(g) determining if there are statistically significant similarities, associations, and differences between the prototype subject/sample peptide fingerprint of the sample identified in step (b) and the peptide fingerprint of the degradation products produced in step (e), concluding that samples from disease Y show characteristic patterns of protein/peptide expression that differ from samples from healthy subjects;
(h) determining if there are statistically significant similarities, associations, and differences between the prototype subject/sample peptide fingerprint of the sample identified in step (b) and the peptide fingerprint of the degradation products produced in step (e), concluding that samples from disease Y show characteristic patterns of protein/peptide expression in common with samples derived from subjects with related disease;
(i) determining if there are statistically significant similarities, associations, and differences between the prototype subject/sample peptide fingerprint of the sample identified in step (b) and the peptide fingerprint of the degradation products produced in step (e), concluding that samples from disease Y show characteristic patterns of protein/peptide expression that differs from samples derived from subjects with unrelated disease Statistically significant similarities may be detected and registered as singular peptide identities or multiple-peptide identities. Determining statistically significant similarities involves using a prototype product peptide fingerprint characteristic of the reaction products resulting from the catalytic activity of a matrix digesting enzyme with it's natural substrate (for example, an MMP12/elastin degradative product peptide fingerprint). Determining statistically significant similarities involves using prototype subject samples in analyses described above to quantitatively and qualitatively measure peptides present within fractions resulting from the analyses procedure. Determining statistically significant similarities involves using prototype samples to establish peptide fingerprint profiles in groups of designated subjects representing characteristic clinical groupings, and the establishment of comparative fingerprints within biofluid or tissue samples.

In preferred methods according to the third aspect of the invention: enzyme X is any one of MMP2, MMP3, MMP7, MMP9, MMP12, and MMP14; the natural substrate is elastin; disease Y is COPD. In particularly preferred methods according to the third aspect of the invention, enzyme X is MMP12 (most preferably human MMP12), the natural substrate is elastin (most preferably human elastin) and disease Y is COPD.

The method according to the third aspect of the invention may be used to determine the presence of a disease Y in humans or in non-human animals. For example, the method may be used during clinical trials involving individual humans or in pre-clinical trials involving non-human animal models. The humans or non-human animals may appear to be healthy or may appear to be diseased. Those that appear to be healthy may be healthy or may be clinically asymptomatic subjects.

A particular method according to the third aspect of the invention is a method to determine the presence of a clinical condition known as disease Y which comprises:
(a) obtaining a biofluid sample or a tissue sample;
(b) analysing the sample to obtain its peptide fingerprint;
(c) mixing enzyme X with its natural substrate in vitro in conditions that allow interaction between enzyme X and its substrate, wherein enzyme X is associated with the clinical condition known as disease Y;
(d) allowing the substrate to be degraded by enzyme X;

(e) analysing the mixture to produce a peptide fingerprint of the degradation products;
(f) comparing the peptide fingerprint of the sample identified in step (b) with the peptide fingerprint of the degradation products produced in step (e), and determining if there are statistically significant similarities between them;
(g) if there are statistically significant similarities between the peptide fingerprint of the sample identified in step (b) and the peptide fingerprint of the degradation products produced in step (e), concluding that the clinical condition known as disease Y is present;
(h) if there are no statistically significant similarities between the peptide fingerprint of the sample identified in step (b) and the peptide fingerprint of the degradation products produced in step (e), concluding that the clinical condition known as disease Y is absent or is being successfully treated.

In a preferred method, the enzyme X is MMP12, the substrate is elastin, and disease Y is COPD, and the peptide fingerprint of the degradation products comprises one or more of the peptides identified in Table 2. In particular the peptide fingerprint of the degradation products comprises at least twenty of the peptides identified in Table 2. More particularly the peptide fingerprint of the degradation products comprises at least ninety of the peptides identified in Table 2. Most particularly the peptide fingerprint of the degradation products comprises at least one hundred and fifty of the peptides identified in Table 2. A preferred peptide fingerprint of the degradation products comprises all the peptides identified in Table 1. Another preferred peptide fingerprint of the degradation products fingerprint comprises all the peptides identified in Table 2.

A preferred method to determine the presence of a clinical condition known as disease Y comprises:
(a) obtaining a biofluid sample or a tissue sample;
(b) analysing the sample to obtain its peptide fingerprint;
(c) comparing the peptide fingerprint of the sample identified in step (b) with a peptide fingerprint comprising peptide products resulting from the degradation of elastin by the enzyme MMP12, wherein the peptide fingerprint comprises one or more of the peptides identified in Table 2, and determining if there are statistically significant similarities between them;
(d) if statistically significant similarities are determined in step (c), concluding that the clinical condition known as disease Y is present;
(e) if no statistically significant similarities are determined in step (c), concluding that the clinical condition known as disease Y is absent or is being successfully treated.

Preferably disease Y is COPD. The peptide fingerprint comprising peptide products resulting from the degradation of elastin by the enzyme MMP12 preferably comprises at least twenty of the peptides identified in Table 2, or at least ninety of the peptides identified in Table 2, or at least one hundred and fifty of the peptides identified in Table 2. Most preferably the peptide fingerprint comprises all the peptides identified in Table 1 or all the peptides identified in Table 2.

In a fourth aspect of the invention we provide a diagnostic test kit for determining the presence of a disease Y which comprises means to compare the peptide fingerprint of a biofluid sample or the peptide fingerprint of a tissue sample with the peptide fingerprint of the degradation products in a mixture of enzyme X with its natural substrate, wherein enzyme X is associated with the clinical condition known as disease Y.

In preferred diagnostic test kits according to the fourth aspect of the invention: enzyme X is any one of MMP2, MMP3, MMP7, MMP9, MMP12, and MMP14; the natural substrate is elastin; disease Y is COPD. In particularly preferred kits according to the fourth aspect of the invention, enzyme X is MMP12 (most preferably human MMP12), the natural substrate is elastin (most preferably human elastin), disease Y is COPD and the peptide fingerprint of the degradation products comprises one or more of the peptides identified in Table 2. In particular the peptide fingerprint of the degradation products comprises at least twenty of the peptides identified in Table 2. More particularly the peptide fingerprint of the degradation products comprises at least ninety of the peptides identified in Table 2. Most particularly the peptide fingerprint of the degradation products comprises at least one hundred and fifty of the peptides identified in Table 2. A preferred peptide fingerprint of the degradation products comprises all the peptides identified in Table 1. Another preferred peptide fingerprint of the degradation products fingerprint comprises all the peptides identified in Table 2.

A preferred diagnostic test kit for determining the presence of a disease Y comprises means to compare the peptide fingerprint of a biofluid sample or the peptide fingerprint of a tissue sample with a substrate fingerprint comprising peptide products resulting from the degradation of elastin by the enzyme MMP12, wherein the substrate fingerprint comprises one or more of the peptides identified in Table 2. Preferably disease Y is COPD. In particular the substrate fingerprint comprises at least twenty of the peptides identified in Table 2. More particularly the substrate fingerprint comprises at least ninety of the peptides identified in Table 2. Most particularly the substrate fingerprint comprises at least one hundred and fifty of the peptides identified in Table 2. A preferred substrate fingerprint comprises all the peptides identified in Table 1. Another preferred substrate fingerprint comprises all the peptides identified in Table 2.

In a fifth aspect of the invention we provide a method to analyse the effect of a drug Z on enzyme X, wherein enzyme X is associated with disease Y, which comprises:
(a) treating a human or non-human animal with the drug Z, wherein the human or non-human animal is suffering from disease Y;
(b) obtaining a biofluid sample or a tissue sample from the human or non-human animal;
(c) analysing the sample to obtain its peptide fingerprint;
(d) mixing enzyme X with its natural substrate in vitro in conditions that allow interaction between enzyme X and its substrate, allowing the substrate to be degraded by enzyme X;
(e) analysing the mixture to produce a peptide fingerprint of the degradation products;
(f) comparing the peptide fingerprint of the sample identified in step (c) with the peptide fingerprint of the degradation products produced in step (e), and determining if there are statistically significant similarities between them;
(g) if there are statistically significant similarities between the peptide fingerprint of the sample identified in step (c) and the peptide fingerprint of the degradation products produced in step (e), concluding that drug Z is not inhibiting enzyme X;
(h) if there are no statistically significant similarities between the peptide fingerprint of the sample identified in step (c) and the peptide fingerprint of the degradation products produced in step (e), concluding that drug Z is inhibiting enzyme X.

The method according to the fifth aspect of the invention may be used during drug discovery and development to ascertain whether the correct drug target is being affected when treating with a particular drug Z. Drug Z may be a drug or a candidate drug compound. The method allows direct study of the effect of drug Z on enzyme X, including the effect of different levels of drug Z. The peptide fingerprint of the degradation products in a mixture of enzyme X with its natural substrate is a biomarker.

In preferred methods according to the fifth aspect of the invention: enzyme X is any one of MMP2, MMP3, MMP7, MMP9, MMP12, and MMP14; the natural substrate is elastin; disease Y is COPD. In particularly preferred methods according to the fifth aspect of the invention, enzyme X is MMP12 (most preferably human MMP12), the natural substrate is elastin (most preferably human elastin) and disease Y is COPD.

A particular method according to a fifth aspect of the invention is a method to analyse the effect of a drug Z on enzyme X, wherein enzyme X is associated with a clinical condition known as disease Y, which comprises:
  a) treating a human or non-human animal with the drug Z, wherein the human or non-human animal is suffering from disease Y;
  b) obtaining a biofluid sample or a tissue sample from the human or non-human animal;
  c) analysing the sample to obtain its peptide fingerprint;
  d) mixing enzyme X with its natural substrate in vitro in conditions that allow interaction between enzyme X and its substrate, allowing the substrate to be degraded by enzyme X;
  e) analysing the mixture to produce a peptide fingerprint of the degradation products;
  f) comparing the peptide fingerprint of the sample identified in step (c) with the peptide fingerprint of the degradation products produced in step (e), in quantitative and qualitative terms of mass, elution time, solubility, time of flight and physical presence or abundance in relationship to other peptides;
  g) determining if there are statistically significant similarities, associations, and differences between the prototype subject/sample peptide fingerprint of the sample identified in step (c) and the peptide fingerprint of the degradation products produced in step (e);
  h) determining whether samples from disease Y show characteristic patterns of protein/peptide expression that differ from samples from healthy subjects;
  i) determining whether samples from disease Y show characteristic patterns of protein/peptide expression in common with samples derived from subjects with related disease;
  j) determining whether samples from subjects with disease Y treated with drug Z do or do not show significant differences in expression patterns in peptide fingerprints compared to subject groups identified in steps (h) and (i).

In a preferred method, the enzyme X is MMP12, the substrate is elastin, and disease Y is COPD, and the peptide fingerprint of the degradation products comprises one or more of the peptides identified in Table 2. In particular the peptide fingerprint of the degradation products comprises at least twenty of the peptides identified in Table 2. More particularly the peptide fingerprint of the degradation products comprises at least ninety of the peptides identified in Table 2. Most particularly the peptide fingerprint of the degradation products comprises at least one hundred and fifty of the peptides identified in Table 2. A preferred peptide fingerprint of the degradation products comprises all the peptides identified in Table 1. Another preferred peptide fingerprint of the degradation products fingerprint comprises all the peptides identified in Table 2.

A preferred method is a method to analyse the effect of a drug Z on the enzyme MMP12 which comprises:
  (a) treating a human or non-human animal with the drug Z, wherein the human or non-human animal is suffering from disease Y;
  (b) obtaining a biofluid sample or a tissue sample from the human or non-human animal;
  (c) analysing the sample to obtain its peptide fingerprint;
  (d) comparing the peptide fingerprint of the sample identified in step (c) with a peptide fingerprint comprising peptide products resulting from the degradation of elastin by the enzyme MMP12, wherein the peptide fingerprint comprises one or more of the peptides identified in Table 2, and determining if there are statistically significant similarities between them;
  (e) if statistically significant similarities are determined in step (d), concluding that drug Z is not inhibiting the enzyme MMP12;
  (f) if no statistically significant similarities are determined in step (d), concluding that drug Z is inhibiting the enzyme MMP12.

Preferably disease Y is COPD. The peptide fingerprint comprising peptide products resulting from the degradation of elastin by the enzyme MMP12 preferably comprises at least twenty of the peptides identified in Table 2, or at least ninety of the peptides identified in Table 2, or at least one hundred and fifty of the peptides identified in Table 2. Most preferably the peptide fingerprint comprises all the peptides identified in Table 1 or all the peptides identified in Table 2.

In a sixth aspect of the invention we provide a diagnostic test kit for analysing the effect of a drug Z on enzyme X which comprises means to compare the peptide fingerprint of a biofluid sample or the peptide fingerprint of a tissue sample with the peptide fingerprint of the degradation products in a mixture of enzyme X with its natural substrate, wherein the sample has been obtained from a human or non-human animal that has been or is being treated with the drug Z.

In preferred diagnostic test kits according to the sixth aspect of the invention: enzyme X is any one of MMP2, MMP3, MMP7, MMP9, MMP12, and MMP14; the natural substrate is elastin; disease Y is COPD. In particularly preferred diagnostic test according to the sixth aspect of the invention, enzyme X is MMP12 (most preferably human MMP12), the natural substrate is elastin (most preferably human elastin), disease Y is COPD and the peptide fingerprint of the degradation products comprises one or more of the peptides identified in Table 2. In particular the peptide fingerprint of the degradation products is comprises at least twenty of the peptides identified in Table 2. More particularly the peptide fingerprint of the degradation products comprises at least ninety of the peptides identified in Table 2. Most particularly the peptide fingerprint of the degradation products comprises at least one hundred and fifty of the peptides identified in Table 2. A preferred peptide fingerprint of the degradation products comprises all the peptides identified in Table 1. Another preferred peptide fingerprint of the degradation products fingerprint comprises all the peptides identified in Table 2.

A preferred diagnostic test kit for analysing the effect of a drug Z on the enzyme MMP12 comprises means to compare the peptide fingerprint of a biofluid sample or the peptide fingerprint of a tissue sample with a substrate fingerprint comprising peptide products resulting from the degradation of elastin by the enzyme MMP12, wherein the substrate fingerprint comprises one or more of the peptides identified in Table 2 and wherein the sample has been obtained from a human or non-human animal that has been or is being treated with the drug Z. In particular the substrate fingerprint comprises at least twenty of the peptides identified in Table 2. More particularly the substrate fingerprint comprises at least ninety of the peptides identified in Table 2. Most particularly the substrate fingerprint comprises at least one hundred and fifty of the peptides identified in Table 2. A preferred substrate fingerprint comprises all the peptides identified in Table 1. Another preferred substrate fingerprint comprises all the peptides identified in Table 2.

From the methods according to the invention, it is possible to generate a disease model (a predictive indicator of disease development) which encompasses the presence/absence, relative abundance, and qualitative/quantitative characteristics of singleton peptides/proteins or groupings of peptides/proteins within each fingerprint. By analysing biofluid or tissue samples over a dynamic time period in relation to specific protein/peptide fingerprints, an association correlation between specific settings of clinical disease and certain specific peptide fingerprints can be established.

In the methods according to the invention, it is preferable to use the following methodology to generate the protein/peptide fingerprints. This methodology provides and results in measurements with optimal resolution and sensitivity.

The preferred methodology is an automated multidimensional liquid phase separation platform technology. The entire platform is operated automatically in a closed operation system, where the multidimensional separating mechanisms are performed in liquid separation phases on chromatographic columns. The interconnections of these separation steps are performed on-line with transfer steps in-between the columns within the workstation. The interfacing in-between the separation mechanisms is provided by chromatographic conditions that allow the analytes to be transferred from one dimension to the next without losses. This is accomplished by the liquid-liquid transfer in-between the dimensions. An operational description of the methodology is given below.

Biofluid samples are introduced into the liquid phase peptide profiling platform and kept at 4° C. thermo stated to ensure stability of the samples over time. The sample is then injected into the first dimensional separation from the auto-injector (column 1). The mechanism in this step is based upon size separation (the separation packing material, of polymer or silica origin, has highly defined pores). In the first dimension, larger sized proteins and biopolymers will be excluded from entering the pores of the beads of the separation material. The analytes of interest, such as peptide analytes, diffuse into the pores and bind to the functionality within the pores. This functionality can be electrostatic charged surfaces or hydrophobic surfaces onto which the peptides are bound. In this way selective enrichment of the peptides occurs as simultaneously the larger sized proteins and biopolymers are excluded and eluted to waste. The column material is then washed a few times with varying eluents in order to exclude interfering components from the sample that has bound to the outer surface as well as to filters and exposed surfaces of the chromatographic system. In this way, the enriched peptide fraction in the pores of the column material is isolated with a high purity.

After the washing steps, a strong eluent is introduced into the next dimension, column 2. In the second dimension, the elution from column 1 is transferred into column 2 on-line and adsorbed on top of the support of column 2. Column 2 is a bead with charged functionality where the separation is performed by electrostatic mechanisms. A gradient elution is used, and the corresponding peptides are separated in eluted fractions. These fractions are next separated in the third dimension by hydrophobicity, whereby the salt is eliminated from the peptide fractions and concentrated using a washing step of aqueous media, followed by elution onto a target plate surface from where the peptide mass sequences is determined.

The fourth dimension of the system utilizes mass spectrometry where the mass, intensity (quantity) of each and every peptide component of all the fractions of the sample is analyzed.

The data generated from the Mass Spectrometer is multifactorial and representative of exact individual samplings at specific time frames of the process steps. The characteristic physical properties of the peptides and proteins which include size, mass, charge, and hydrophobicity constants result in individual signature profiles for each peptide or protein. The mass spectrophotometer instrument detects and records these characteristics as files with three headings: Fraction, Mass/z and Intensity.

The mass values are typically recorded to the $4^{th}$ decimal point, however, in practice for presentation, these are rounded off to the nearest digital value.

The process for establishing statistical significance to the associations of peptides with given fingerprints, or between individual fingerprints or groups of fingerprints is based upon constants of a data matrix which is constructed from the Fraction, mass/z and intensity values of each peptide. The data matrix is derived by the combinations of fractions and masses present in each subject sample, and where the intensities are summed for each such mass and fraction combination. The data matrix then becomes:

$$d = \frac{\mathit{diff}}{S_0 + S}$$

where $I_{1,1}$ etc are the summed intensities. Subjects are normalised by equating the total sum of intensities per subject.

A Java code calculates a regularized, t-statistic that minimizes the false positive and false negative rates, following the theory in Broberg (2003, *Genome Biology*, 4(6):R41). In practice one starts out with a top list size or a number of practical top list sizes, and the task is to find an optimal size in the range given and to populate that list with as many true positives as possible. The test statistic used has the form pioneered by Tusher et al (2001, *Proc. Natl. Acad. Sci. USA*, 98: 5116-5121)

$$d = \frac{\mathit{diff}}{S_0 + S}$$

where diff is an effect estimate, e.g. a group mean difference, S is a standard error, and $S_0$ is a regularizing constant. In the two sample case putting $S_0$=0 will yield the equal variance t-test. Using estimates of the false positive and false negative rates an optimisation procedure minimises the criterion C=√(FP²+FN²) over a lattice of possible values of $S_0$ (given by percentiles in the distribution of S) and the length of the top list.

The output include group means, p-values for the comparison, the false positive rate and false negative rate that would arise from including the current Fraction×Mass and all with smaller p-values. The cut-off is chosen as to minimise the false positive and false negative rates.

The resulting mass spectra data, peptide mass, peptide fraction and peptide identity is generated by statistical comparisons between for example COPD and healthy subjects. The digital mass unit is grouped into bins with +/−0.5 mass units on either side of the detected mass, and combined with a given peptide fraction. Next the bin intensities are summed to produce an extrapolated identity for each and every fragment. The total bin numbers used in the statistical analysis were typically between 10.000-20.000. The mass fragments are then compared by subject groupings such as for example COPD or healthy subjects. The statistical analysis is based on 40-50 fractions collected from each subject. The cycle time generating the 40-50 peptide fractions is less than 5 hours.

The mass fragments of the peptides described in Example 1 and Example 2 below could not be identified in any of the prototype 20 healthy subjects tested using this methodology.

Integrated process steps for biomarker identification is essential, containing the following four process defining corner stones; 1/high quality biomedical clinical material, 2/Technology platform for qualitative and quantitative determination of peptides, 3/In Vitro assay where qualitative and quantitative analysis of for example, peptide/peptides products resulting from the reaction with MMP-12 enzyme, with human Elastin as the substrate, 4/A statistical method for relating multiple sets of peak identities to prototype fingerprints and to differential expression of these peptides and peptide fingerprints within and between designated subject groups. This is preferred way of analysing the data that allows to analyse the biomarker peptides that are likely associated with COPD patient urine (Scheme D).

Each of the four process corner stones are interdependent and required in order to determine biomarker peptides by differential quantitation between healthy and COPD subjects, relating it to for example, the MMP-12 enzyme function/activity derived peptides from Elastin. The preferred method may also be used to determine and detect the natural elastin breakdown products resulting from the cleavage of elastin with naturally or designed elastolytic specific enzymes including MMP 2, MMP3, MMP7, MMP9, and MMP14.

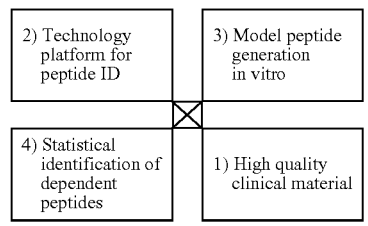

Scheme D: interdependence of process cornerstones

The invention is illustrated by the following non-limiting examples.

Example

The peptide fragments of elastin, which are the result from the enzymatic digestion of human elastin by human MMP 12, were first identified under laboratory conditions using a model in vitro system for generating unit length peptides and peptide fingerprints of the proteolysis of elastin by this MMP12 enzyme. These peptides were then collected and fractionated on a series of chromatography columns in order to isolate the peptides for identification. The peptides were then identified as unit atomic mass entities using MALDI-TOF mass spectrometry spectra. For each fraction of column separated peptides, the mass of each entity, and the mass intensity of each entity were recorded and stored into databases. A statistical software program was used to analyze the profile of atomic mass unit identities from all fractions analysed by MS. A consensus atomic mass identity was assigned for a set of landmark elastin peptides associated with MMP12 enzymatic degradation. A first non-inclusive set of 97 elastin derived peptides, also known as a peptide fingerprint, is provided in Table 1. A second non-inclusive set of 185 elastin derived peptides, also known as a peptide fingerprint, is provided in Table 2. The set of 185 peptides shown in Table 2 includes the set of 97 peptides shown in Table 1.

Tables 1 and 2 provide the identities of landmark peptides which can be used as reference points for discovering and or identifying peptides with similar or nearly similar physical-chemical properties in other complex mixtures of proteins. The Tables provide the identities of landmark peptides which can be used as reference points for discovering and or identifying peptides of similar characteristic that are present in human clinical samples. This further provides the identities of landmark peptides which can be used as reference points for discovering and or identifying the exact amino acid sequence identity of these same peptide entities. This provides the identities of landmark peptides which can be used as reference points for discovering and or identifying the presence, absence, and relative abundance of individual peptides or any groupings of these peptides in clinical samples from healthy subjects or subjects with clinical conditions which are associated with the breakdown of human elastin, and the subsequent groupings of subjects based upon these fingerprints or any combination of the peptides present in these samples.

Experimental Procedure

The following method was used. An MMP-12 in vitro assay has been developed in order to make peptide annotations that are directly assigned to the MMP-12 activity. These annotations represent peptide masses that are specific to degrading of human elastin by human MMP-12 proteolytic activity and are used to establish signatures of peptide fingerprints that can be measured and matched with signature peptide profiles present within biofluid samples sampled from both healthy subjects and subjects with clinical conditions such as COPD. Other elastin specific proteolytic enzymes such as MMP2, MMP3, MMP7, MMP9, and MMP14 will produce separate and distinct peptide products from the elastin substrate. The assay is run as follows; human lung elastin is used as the substrate in the in vitro assay reaction with human MMP-12. The insoluble human elastin is washed using a 100 mM TRIS-HCL buffer pH 7.5 containing 0.1 M NaCl and 10 mM CaCl2, and then centrifuged in-between repeated washing steps. Next, 1.2 mg elastin is re-suspended in the assay buffer 100 mM TRIS-HCL buffer pH 7.5 containing 0.1 M NaCl and 10 mM CaCl2 and 60 μg human MMP-12. Incubation was made at 37° C. for 7 hours where the elastin was degraded by the enzyme MMP12. The proteolysis process was stopped by the addition of iodoacetamide.

After digestion, the samples were analysed directly or kept at −80° C. in the freezer. The samples were analysed by thawing of samples in room temperature, and a sample preparation step was performed using a reversed phase preparation step. The sample was then eluted from the preparation by an acetonitrile elution step onto the MALDI-TOF target plate. Cyano-4-hydroxycinnamic acid (ACHA) was added as the matrix for crystal formation and run on the MALDI-TOF mass spectrometer where a peptide fingerprint of the MMP12/elastin degradation products was identified and annotated.

The specific experimental conditions used in order to generate differentially displayed peptides in human urine samples from healthy subjects and COPD patients was made as follows.

The urine biofluid was obtained and collected from subjects by normal urination and thereafter aliquoted and frozen at −80° C. The frozen urine was thawed in room temperature, pH adjusted to 2.5 with orthophosphoric acid and processed for HPLC separations. The urine samples were introduced into a two-dimensional chromatography system in which the first separation mechanism utilised was size exclusion chromatography. The cut-off of the column material was designated as 15 kDa. The fractionations resulting from 1) the size exclusion column separation step were transferred on-line to a 2) cation-exchange column step where the peptides/proteins were separated based upon charge. These fractions were then transferred to a 3) reversed phase separation column step where all interfering matrix components present in the sample were eliminated. The third dimension fractions were spotted down onto a MALDI target plate by a robotic feeder that added the MALDI matrix to the peptide/protein sample spots. Next the MALDI sample plate was inserted into the MALDI-TOF mass spectrometer instrument and irradiated to peptide produce fragments which were then analysed according to the exact mass, quantity and isotope resolution of each individual MALDI-TOF peptide spectrum.

The elastin peptide fingerprint generated by MMP12 digestion under laboratory conditions, and described above, is used as a reference landmark for finding identical or nearly identical homologous peptides within clinical biofluids.

Elastin peptide fragments or the elastin peptide fingerprint are identified in the urine of a patient with Chronic obstructive Pulmonary Disease (COPD). This patient was previously identified within a clinical setting as having COPD. In this example the patient showed abnormal respiratory function tests, as revealed by a low FEV1 score. This patient further showed evidence of pulmonary alveolar hyper-inflation and emphysema using CT imaging. This patient further showed evidence of elastin protein destruction within the parenchyma of the lung by histology examination of the lung, and by using a method for identifying elastin protein within lung tissue by immunohistochemistry with an antibody specific for human elastin, and specific for a hexamer epitope of human elastin and tropoelastin. This patient further showed histological evidence of alveolitis and alveolar macrophage accumulation in areas of lung, located adjacent to elastin expression and elastin degradation. This patient further showed histological evidence that the same alveolar located macrophages were activated to express a marker of activation, CD68, within tissue by immunohistochemistry of sections of lung tissue with an antibody specific for CD-68. This patient further showed histological evidence that the same alveolar located macrophages were activated to express human MMP-12 within tissue by immunohistochemistry of sections of lung tissue with an antibody specific for human MMP-12. This patient was a member of a group of 20 patients under study. The findings described above were not unique to this single COPD patient. The findings described above were a common finding among the 20 study COPD patients.

The following method was used:

1) A healthy human bio fluid sample was obtained; We define healthy in this example as a living adult person aged 20-80, without symptoms of disease, without current clinical condition, not being treated for a clinical condition with medication or prescribed drugs, without at risk behaviour for developing disease such as smoking, drug abuse, alcoholism, overweight, or without a diagnosed genetic disposition for disease in later onset of life for example. We define biofluid here as any sample of human clinical material in solution form. This may include blood, serum, plasma, saliva, ravages, tears, urine, seminal fluid, joint fluid, aqueous humor, washings of cavities or sinuses, the soluble form of tissue preparations, the soluble form of organ preparations, or sweat, for example. The samples may be derived from singular subjects or pools of singular samples from multiple subjects. In this example the healthy biofluid was urine.

2). The healthy urine sample was analysed to produce a healthy peptide fingerprint; We define analysed for example, as any combination of the steps of sample selection, preparation, separation, identification, annotation, retrieval of stored data, and comparisons of data from the body of this application, the examples provided in this application, the claims of this application. We define fingerprint in this example as a identifiable singular peptide constituent of a native protein, and/or, which may be or not combined with other identifiable singular peptide constituent of a native protein, and or the sum total of all identifiable singular peptides which can be grouped together and as such that grouping becomes an entity itself. We define identifiable as the fraction, mass, and intensity of singular peptide entities. We further define mass as the unique MS mass assignment of an identifiable singular peptide, the derived mass of collected identifiable singular peptide entities, and or the derived mass of collected identifiable singular peptide entities in combination.

3) A diseased human bio fluid sample was obtained from a diseased individual. Diseased in this example is defined as an adult person aged 2080, with or without clinical symptoms or presentation of disease, and/or with a clinical at risk behaviour for developing disease such as smoking, drug abuse, alcoholism, overweight, with or without a diagnosed genetic disposition for disease in later onset of life. For example, patients with a clinical diagnoses of COPD, or patients at risk for developing (COPD); We define at risk for disease for example, as a current smoker of tobacco or other medicinal herb, or a person who has ever smoked, or as a person who has smoked and quit smoking, irrespective of time frame in relation to the sampling of these same patients for study. We further define at risk for disease as any person with deficiencies in the expression or the regulation of expression of alpha-1-anti-trypsin or related naturally occurring biochemical molecules, or any or any biological entity related to the expression or function of alpha-1-anti-trypsin or related naturally occurring biochemical molecules. The diseased individual in this example was a subject who showed signs of the onset or progression of Chronic obstructive Pulmonary Disease (COPD). We further may characterize COPD patients as subjects which show elastin breakdown using histological analysis, or immunohistochemistry analysis of pulmonary tissue samples We further may characterize COPD patients as subjects which show alveolitis, airway hyperinflation, or emphysema using X-ray imaging (HRCT,CT), histological analysis, or immuno-histochemistry analysis of pulmonary tissue samples. We further may characterize COPD patients as subjects which show evidence of activated macrophages within pulmonary tissue samples using histology and immunohistochemistry with antibodies specific for the detection of products of genes expressed by activated macrophages. In this example the patient showed histological evidence of pulmonary airway space enlargement, emphysema, and destruction of pulmonary elastin integrity. The example further showed evidence of activated alveolar macrophages near sites of pulmonary elastin destruction.

We define diseased biofluid here as any sample of human clinical material in solution form taken from patients who fulfil all or parts of the criteria of the definition of disease as above. This may include blood, serum, plasma, saliva, ravages, tears, urine, seminal fluid, joint fluid, aqueous humor, washings of cavities or sinuses, the soluble form of tissue preparations, the soluble form of organ preparations, or sweat, for example. The samples may be derived from singular patients or pools of singular samples from multiple patients. In this example the biofluid was urine.

4) The diseased sample was analysed to produce a diseased peptide fingerprint; We define fingerprint in this example as a identifiable singular peptide constituent of a native protein, and/or, which may be or not combined with other identifiable singular peptide constituent of a native protein, and or the sum total of all identifiable singular peptides which can be grouped together and as such that grouping becomes an entity itself. We define identifiable as the fraction, mass, and intensity of singular peptide entities. We further define mass as the unique MS mass assignment of an identifiable singular peptide, the derived mass of collected identifiable singular peptide entities, and or the derived mass of collected identifiable singular peptide entities in combination.

Summary of Experimental Procedure
1) a healthy human bio fluid sample was obtained;
2) the healthy urine sample was analysed to produce a healthy peptide fingerprint
3) A diseased human bio fluid sample was obtained from a diseased individual;
4) The diseased sample was analysed to produce a diseased peptide fingerprint;
5) the healthy peptide fingerprint was compared to the diseased peptide fingerprint to identify the set of peptides found only in the diseased peptide fingerprint;
6) The diseased set of peptides identified in step (5) was compared with the peptide fingerprint of the degradation products produced in step (8).

Description of the Experimental Procedure

The specific experimental conditions used in order to generate differentially displayed peptides in human urine samples from healthy subjects and COPD patients was made as follows;

The biofluid was sampled from patients and thereafter aliquoted and frozen at −80° C.

The frozen urine was thawed in room temperature, pH adjusted to 2.5 with orthophosphoric acid and processed for HPLC separations. The urine samples were introduced into a three-dimensional chromatography system where the fire separation mechanism utilised was size exclusion chromatography. The cut-off of the column material was approximately 15 kDa. The fractionations resulting from the size exclusion separation step is next transferred on-line to a cation-exchange column chromatography step where the peptides/proteins were separated based upon charge. These fractions are then transferred to a reversed phase separation step where all interfering matrix components present in the sample is eliminated, this is the third dimensional separation. The third dimension fractions were spotted down onto a MALDI target plate by a robotic feeder robotic feeder that added the MALDI matrix to the peptide/protein sample spots. Next the MALDI sample plate was inserted into the MALDI-TOF mass spectrometer instrument and irradiated to peptide produce fragments which were then analysed according to the exact mass, quantity and isotope resolution of each individual MALDI-TOF peptide spectrum.

Tables

Table 1 shows the MS atomic mass unit identities of 97 elastin peptides resulting from MMP12 digestion and separation by column chromotagraphy. Table 2 shows the MS atomic mass unit identities of 185 elastin peptides resulting from MMP12 digestion and separation by column chromotagraphy. To generate each set of peptides, fractions of column eluates containing separated peptides were applied to MS, identified, annotated, and then placed into a database for statistical analysis.

Figures

FIG. 1 and FIG. 2 illustrate two examples where we have determined the qualitative and quantitative differences between the peptide fingerprints of healthy subjects and COPD patients. Shown are data of putative elastin peptides detected in the urine samples, respectively. In FIGS. 1A and 2A, are shown examples of the peptides found present in the urine biofluid from COPD patients, due to active MMP-12 degradation, while FIGS. 1B and 2B representing equivalent fractions from healthy subjects do not hold these peptides. The absence values of these peptides in the healthy subjects were based upon the lowest level of quantification that MALDI instrumentation offers.

FIG. 1 shows the mass spectrum generated from a given liquid phase separation fraction where: FIG. 1A shows the peptide fingerprint in a human urine fraction from a COPD sufferer; FIG. 1B shows the peptide fingerprint in a healthy subject; FIG. 1C shows the peptide fingerprint in a MMP-12+ elastin mixture, 2.5 h incubation.

FIG. 2 is another example showing the mass spectrum generated from a given liquid phase separation fraction where: FIG. 2A shows the peptide fingerprint in a human urine fraction from a COPD sufferer; FIG. 2B shows the peptide fingerprint in a healthy subject; FIG. 2C shows the peptide fingerprint in a MMB-12+ elastin mixture, 2.5 h incubation.

Results shown in FIG. 1 present the mass spectrum generated from a given liquid phase separation fraction with peptides having a specific given chemical-physical property peptide. In FIG. 1A the resulting mass spectrum shows the presence of the mass peak of 1094.60 in COPD patients that corresponds to a MMP-12 enzymatic product with elastin as a substrate. FIG. 1B illustrates the resulting mass spectrum from healthy volunteers where the 1094.60 mass of the peptide peak is not qualitatively distinguishable from the background signals. These data are statistically significant when compared within the diseased and healthy patient groups.

FIG. 2A shows that the peptide peak corresponding to a mass of 1285.7 is present in a human urine fraction from a COPD sufferer. FIG. 2B shows that this peptide peak is absent from the mass spectrum of the healthy individual. These data are statistically significant when compared within the diseased and healthy patient groups.

TABLE 1

| Peptide number | Peptide mass |
| --- | --- |
| 1 | 772.4 |
| 2 | 798.4 |
| 3 | 802.4 |
| 4 | 817.5 |
| 5 | 823.4 |
| 6 | 824.4 |
| 7 | 865.4 |
| 8 | 874.5 |
| 9 | 878.5 |
| 10 | 904.4 |

TABLE 1-continued

| Peptide number | Peptide mass |
|---|---|
| 11 | 937.5 |
| 12 | 944.5 |
| 13 | 951.5 |
| 14 | 977.5 |
| 15 | 1027.5 |
| 16 | 1072.6 |
| 17 | 1073.6 |
| 18 | 1089.5 |
| 19 | 1094.6 |
| 20 | 1107.6 |
| 21 | 1114.6 |
| 22 | 1137.6 |
| 23 | 1141.6 |
| 24 | 1142.6 |
| 25 | 1145.6 |
| 26 | 1155.6 |
| 27 | 1171.6 |
| 28 | 1185.7 |
| 29 | 1193.6 |
| 30 | 1199.6 |
| 31 | 1216.6 |
| 32 | 1232.6 |
| 33 | 1237.6 |
| 34 | 1242.7 |
| 35 | 1254.7 |
| 36 | 1255.9 |
| 37 | 1262.6 |
| 38 | 1265.7 |
| 39 | 1285.7 |
| 40 | 1287.7 |
| 41 | 1291.7 |
| 42 | 1296.7 |
| 43 | 1298.7 |
| 44 | 1299.7 |
| 45 | 1314.7 |
| 46 | 1320.8 |
| 47 | 1322.7 |
| 48 | 1331.7 |
| 49 | 1347.7 |
| 50 | 1352.7 |
| 51 | 1363.7 |
| 52 | 1368.8 |
| 53 | 1369.0 |
| 54 | 1370.7 |
| 55 | 1379.6 |
| 56 | 1402.8 |
| 57 | 1424.8 |
| 58 | 1440.7 |
| 59 | 1455.8 |
| 60 | 1469.8 |
| 61 | 1477.8 |
| 62 | 1484.8 |
| 63 | 1505.8 |
| 64 | 1508.9 |
| 65 | 1519.8 |
| 66 | 1520.8 |
| 67 | 1524.8 |
| 68 | 1536.8 |
| 69 | 1542.8 |
| 70 | 1570.7 |
| 71 | 1596.8 |
| 72 | 1599.8 |
| 73 | 1613.9 |
| 74 | 1644.8 |
| 75 | 1666.9 |
| 76 | 1670.9 |
| 77 | 1687.9 |
| 78 | 1696.9 |
| 79 | 1702.2 |
| 80 | 1706.8 |
| 81 | 1718.9 |
| 82 | 1758.9 |
| 83 | 1762.9 |
| 84 | 1763.9 |
| 85 | 1770.0 |
| 86 | 1832.9 |
| 87 | 1840.0 |
| 88 | 1851.0 |
| 89 | 1885.0 |
| 90 | 1920.0 |
| 91 | 1929.8 |
| 92 | 1942.0 |
| 93 | 1998.1 |
| 94 | 2168.1 |
| 95 | 2367.2 |
| 96 | 2620.3 |
| 97 | 2823.5 |

TABLE 2

| peptide number | peptide mass |
|---|---|
| 1 | 772.4 |
| 2 | 798.4 |
| 3 | 799.4 |
| 4 | 802.4 |
| 5 | 817.5 |
| 6 | 823.4 |
| 7 | 824.4 |
| 8 | 826.4 |
| 9 | 842.4 |
| 10 | 865.4 |
| 11 | 874.5 |
| 12 | 878.5 |
| 13 | 880.5 |
| 14 | 887.5 |
| 15 | 904.4 |
| 16 | 937.5 |
| 17 | 944.5 |
| 18 | 951.5 |
| 19 | 977.5 |
| 20 | 994.5 |
| 21 | 1009.5 |
| 22 | 1027.5 |
| 23 | 1034.5 |
| 24 | 1038.6 |
| 25 | 1072.6 |
| 26 | 1073.6 |
| 27 | 1085.5 |
| 28 | 1089.5 |
| 29 | 1094.6 |
| 30 | 1107.6 |
| 31 | 1114.6 |
| 32 | 1116.5 |
| 33 | 1132.5 |
| 34 | 1137.6 |
| 35 | 1138.6 |
| 36 | 1141.6 |
| 37 | 1142.6 |
| 38 | 1145.6 |
| 39 | 1147.6 |
| 40 | 1155.6 |
| 41 | 1169.6 |
| 42 | 1171.6 |
| 43 | 1177.6 |
| 44 | 1185.7 |
| 45 | 1188.6 |
| 46 | 1193.6 |
| 47 | 1196.6 |
| 48 | 1199.6 |
| 49 | 1212.6 |
| 50 | 1216.6 |
| 51 | 1232.6 |
| 52 | 1237.6 |
| 53 | 1242.7 |
| 54 | 1254.7 |
| 55 | 1255.9 |
| 56 | 1262.6 |
| 57 | 1265.7 |
| 58 | 1282.7 |
| 59 | 1285.7 |
| 60 | 1287.7 |
| 61 | 1291.7 |

TABLE 2-continued

| peptide number | peptide mass |
|---|---|
| 62 | 1292.6 |
| 63 | 1296.7 |
| 64 | 1298.7 |
| 65 | 1299.7 |
| 66 | 1308.7 |
| 67 | 1314.7 |
| 68 | 1318.9 |
| 69 | 1320.8 |
| 70 | 1321.7 |
| 71 | 1322.7 |
| 72 | 1325.7 |
| 73 | 1331.7 |
| 74 | 1347.7 |
| 75 | 1352.7 |
| 76 | 1357.7 |
| 77 | 1363.7 |
| 78 | 1368.8 |
| 79 | 1369 |
| 80 | 1370.7 |
| 81 | 1379.6 |
| 82 | 1402.8 |
| 83 | 1424.8 |
| 84 | 1440.7 |
| 85 | 1443.8 |
| 86 | 1445.8 |
| 87 | 1448.8 |
| 88 | 1455.8 |
| 89 | 1469.8 |
| 90 | 1476.7 |
| 91 | 1477.8 |
| 92 | 1479.7 |
| 93 | 1480.8 |
| 94 | 1484.8 |
| 95 | 1485.8 |
| 96 | 1505.8 |
| 97 | 1508.9 |
| 98 | 1511.8 |
| 99 | 1519.8 |
| 100 | 1520.8 |
| 101 | 1524.8 |
| 102 | 1527.8 |
| 103 | 1536.8 |
| 104 | 1542.8 |
| 105 | 1557.8 |
| 106 | 1558.8 |
| 107 | 1570.7 |
| 108 | 1583.8 |
| 109 | 1588.7 |
| 110 | 1596.8 |
| 111 | 1599.8 |
| 112 | 1612.9 |
| 113 | 1613.9 |
| 114 | 1628.8 |
| 115 | 1631.8 |
| 116 | 1644.8 |
| 117 | 1656.9 |
| 118 | 1665.8 |
| 119 | 1666.9 |
| 120 | 1670.9 |
| 121 | 1671.9 |
| 122 | 1676.9 |
| 123 | 1677.9 |
| 124 | 1687.9 |
| 125 | 1688.8 |
| 126 | 1696.9 |
| 127 | 1698.9 |
| 128 | 1702.2 |
| 129 | 1704.9 |
| 130 | 1705.9 |
| 131 | 1706.8 |
| 132 | 1712.9 |
| 133 | 1718.9 |
| 134 | 1724.9 |
| 135 | 1727.9 |
| 136 | 1758.9 |
| 137 | 1759.9 |
| 138 | 1762.9 |
| 139 | 1763.9 |
| 140 | 1770 |
| 141 | 1773.9 |
| 142 | 1778.9 |
| 143 | 1832.9 |
| 144 | 1833.9 |
| 145 | 1840 |
| 146 | 1841.0 |
| 147 | 1851 |
| 148 | 1863.0 |
| 149 | 1879.0 |
| 150 | 1885 |
| 151 | 1904.1 |
| 152 | 1907.0 |
| 153 | 1920 |
| 154 | 1924.0 |
| 155 | 1925.1 |
| 156 | 1926.1 |
| 157 | 1929.8 |
| 158 | 1936.0 |
| 159 | 1942 |
| 160 | 1945.8 |
| 161 | 1998.1 |
| 162 | 2034.1 |
| 163 | 2055.1 |
| 164 | 2098.0 |
| 165 | 2162.2 |
| 166 | 2168.1 |
| 167 | 2235.1 |
| 168 | 2305.1 |
| 169 | 2310.1 |
| 170 | 2320.3 |
| 171 | 2323.2 |
| 172 | 2327.2 |
| 173 | 2351.2 |
| 174 | 2367.2 |
| 175 | 2398.2 |
| 176 | 2405.2 |
| 177 | 2449.2 |
| 178 | 2476.2 |
| 179 | 2510.2 |
| 180 | 2620.3 |
| 181 | 2715.3 |
| 182 | 2759.4 |
| 183 | 2823.5 |
| 184 | 3356.7 |
| 185 | 3371.7 |

What we claim is:

1. A set of purified peptides comprising peptide products resulting from the degradation of elastin by the enzyme matrix metalloproteinase 12 (MMP 12), wherein the set of peptides comprises at least twenty of the peptides identified in Table 2.

2. The set of purified peptides as claimed in claim 1 which comprises at least ninety of the peptides identified in Table 2.

3. The set of purified peptides as claimed in claim 1 which comprises at least one hundred and fifty of the peptides identified in Table 2.

4. The set of purified peptides as claimed in claim 1 which comprises all the peptides identified in Table 2.

5. A set of purified peptides comprising purified peptide products resulting from the degradation of elastin by the enzyme matrix metalloproteinase 12 (MMP12), wherein the set of peptides comprises all the peptides identified in Table 1.

* * * * *